US006991608B2

(12) United States Patent
Young et al.

(10) Patent No.: US 6,991,608 B2
(45) Date of Patent: Jan. 31, 2006

(54) MEDICAL ASSEMBLY

(75) Inventors: John Young, Staten Island, NY (US); Kirk D. Swenson, North Caldwell, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 445 days.

(21) Appl. No.: 10/406,398

(22) Filed: Apr. 3, 2003

(65) Prior Publication Data

US 2004/0199085 A1  Oct. 7, 2004

(51) Int. Cl.
*A61D 5/00* (2006.01)

(52) U.S. Cl. ..................................... 600/581
(58) Field of Classification Search ............... 600/573, 600/576–583; 604/263, 194, 158, 195, 506, 604/528, 168.01, 232, 208, 209, 220, 177
See application file for complete search history.

(56) References Cited

U.S. PATENT DOCUMENTS

| | | |
|---|---|---|
| 4,592,744 A | 6/1986 | Jagger et al. |
| 4,838,870 A | 6/1989 | Haber et al. |
| 4,915,702 A | 4/1990 | Haber |
| RE33,585 E | 5/1991 | Haber et al. |
| 5,066,287 A | 11/1991 | Ryan |
| 5,067,490 A | 11/1991 | Haber |
| 5,070,885 A | 12/1991 | Bonaldo |
| RE33,952 E | 6/1992 | Bonaldo |
| 5,117,837 A | 6/1992 | Wanamaker et al. |
| 5,259,392 A | 11/1993 | Schmitt |
| 5,337,756 A | 8/1994 | Barbier et al. |
| 5,346,475 A | 9/1994 | Gregorio |
| 5,356,392 A | 10/1994 | Firth et al. |
| 5,554,166 A | 9/1996 | Lange et al. |
| RE35,539 E | 6/1997 | Bonaldo |
| 5,755,673 A | 5/1998 | Kinsey |
| 5,797,490 A | 8/1998 | Fujii et al. |
| 5,876,355 A | 3/1999 | Suzuki |
| 5,891,052 A | 4/1999 | Simmons |
| 5,938,622 A | 8/1999 | Chen |
| 5,961,473 A | 10/1999 | Fujii et al. ................. 600/576 |
| 6,146,337 A | 11/2000 | Polidoro et al. |
| 6,186,960 B1 | 2/2001 | Trippe et al. .............. 600/576 |
| 6,264,620 B1 | 7/2001 | Shieh |
| 6,280,401 B1 | 8/2001 | Mahurkar |

FOREIGN PATENT DOCUMENTS

WO   WO99/23947   5/1999

*Primary Examiner*—Max F. Hindenburg
*Assistant Examiner*—Brian Szmal
(74) *Attorney, Agent, or Firm*—Kirk Miles, Esq.; Webb Law Firm

(57) ABSTRACT

A medical needle device includes a needle assembly, a hollow needle assembly holder, and a one-way rotational collar. The needle assembly includes a needle hub supporting a needle. The needle hub has a proximal end and a distal end. The hollow needle assembly holder has a proximal end and a distal end. The distal end of the holder defines an opening communicating with the interior of the holder. The one-way rotational collar is rotatably received in the opening in the holder for connecting the needle assembly to the holder. The collar defines a needle assembly receiving socket. The proximal end of the needle hub is received in the socket. The collar is configured to co-act with the interior of the holder such that the collar and needle assembly can rotate in only one direction relative to the holder.

49 Claims, 29 Drawing Sheets

MEDICAL ASSEMBLY

BACKGROUND OF THE INVENTION

1. Field of the Invention

The present invention relates to a medical needle device for use in blood collection procedures and, more particularly, a medical needle device that prevents or hinders users from removing a needle assembly from the device during normal use.

2. Description of Related Art

Disposable medical needle devices having piercing elements are typically used for administering a medication or withdrawing a fluid, such as blood, from the body of the patient. Such piercing elements include blood collecting needles, fluid handling needles, and assemblies thereof. Current medical practice requires that fluid collection containers and needle assemblies used in such devices be inexpensive and readily disposable. Often, existing blood collection devices employ some form of durable, reusable holder on which detachable and disposable needle assemblies and fluid collection containers are mounted. A blood collection system of this nature may be assembled prior to use and then disassembled after use.

A popular design configuration of known blood collection systems includes a double-ended needle assembly, an evacuated fluid collection tube, and a holder for maintaining the needle assembly and the fluid collection tube in fixed relation. The double-ended needle assembly includes a needle having a bore extending therethrough. A hub is located at one end of the needle and includes an opening communicating with the bore in the needle. The evacuated fluid collection tube includes a puncturable stopper at one end. In this type of blood collection system, the holder typically has a housing at one end for receiving the needle assembly, which is comprised of the needle and hub. The holder has a hollow body with an opening at an opposite end thereof for receiving the fluid collection tube. The needle assembly is rigidly received within the housing of the holder such that a first or distal end of the needle extends outward from the holder for puncturing the vein of a patient. At the opposite end, the needle extends into the hollow body. To assemble the blood collection system, the needle assembly is inserted into the housing and the evacuated fluid collection tube is partially inserted through the open end of the hollow body. To draw a blood specimen from the patient using one of these systems, the distal exposed end of the needle is inserted into a patient's vein and the collection tube is fully inserted into the holder until the second or proximal end of the needle pierces the puncturable stopper of the fluid collection tube, thereby allowing fluid communication between the interior of the fluid collection tube and the bore of the needle. Blood will then be drawn through the needle into the evacuated fluid collection tube. After drawing a specimen, the blood collection tube is removed so that blood contained therein may be analyzed and the needle assembly detached for disposal.

A prior art blood collection device set known in the art is disclosed by U.S. Pat. No. 5,066,287 to Ryan. This patent discloses a rear adapter assembly used as part of a blood collection set. The rear adapter assembly includes a rear blood tube holder and a male connector that is inserted into the holder. The male connector includes a ratcheted ramp with a plurality of ratchet teeth that engage with an annular internal ratchet located within the holder. In particular, the annular internal ratchet is provided on a holder ramp formed in the front wall of the holder. The ratcheting connection between the male connector and holder is provided to make a permanent connection between these two elements.

Another blood collection device known in the art is disclosed by U.S. Pat. No. 5,117,837 to Wanamaker, et al. This patent is directed to a blood collection device that is generally comprised of a needle assembly, a needle holder, and an evacuated sample collection tube. The needle assembly includes a hub and an adapter. These elements are connected together by a threaded connection. The adapter includes a crown defining a plurality of serrated teeth. The serrated teeth on the crown are adapted to cooperate with serrated teeth formed on a lid, which covers the distal end of the holder. The adapter snap-fits into engagement with the lid covering the distal end of the holder.

The foregoing patents disclose medical devices wherein a needle assembly may be removed from a needle holder at any time during or after a medical procedure. With the concern over viral infections that are easily transferable due to accidental needle sticks, it is particularly desirable to minimize the risk of such needle sticks by discouraging users from attempting to remove a needle assembly from a needle holder after a medical procedure involving the withdrawal of bodily fluids.

Accordingly, a need exists for a medical needle device that prevents or hinders users from removing a used needle assembly from a needle holder during its normal use.

SUMMARY OF THE INVENTION

The present invention is a holder for supporting a needle assembly for use in a blood collection procedure. The holder includes a hollow holder body having a generally open proximal end and a partially enclosed distal end. The distal end of the holder body defines an opening communicating with the interior of the holder body. A one-way rotatable collar is in rotational communication with the opening in the holder body. The collar includes a needle assembly receiving socket for receiving a needle assembly for connection with the holder body. The collar is configured to co-act with the interior of the holder body such that the collar can rotate in only one direction relative to the holder body when a needle assembly is received in the socket.

The one-way rotational movement of the collar relative to the holder may be provided through a number of arrangements. For example, the collar may include a first disc portion rotatably received in the opening in the holder body and a second disc portion extending into the interior of the holder body. The second disc portion may include at least one locking pawl configured to engage at least one ratchet tooth formed on an inner wall of the holder body for permitting the one-way rotational movement of the collar relative to the holder body. The first disc portion may include a lip in engagement with the distal end of the holder for rotatably connecting the collar to the holder body. The socket may be internally threaded such that a separate needle assembly can be held in the socket by a threaded connection. The locking pawl and the ratchet tooth may be configured to engage when such a needle assembly is threaded into the socket. The locking pawl and the ratchet may be further configured to allow the locking pawl to slip over the ratchet tooth to rotate the collar when an attempt is made to unthread such a needle assembly from the socket.

Alternatively, the second disc portion of the collar may include at least one locking tooth configured to engage at least one ratchet pawl formed on an inner wall of the holder body for permitting the one-way rotational movement of the collar relative to the holder body. In yet a further alternative arrangement, the second disc portion may include at least one locking tooth configured to engage at least one ratchet tooth formed on an inner wall of the holder for permitting the one-way rotational movement of the collar relative to the holder body. The second disc portion may further include at least one locking tooth facing the inner surface of the distal end of the holder body and be configured to engage at least one ratchet tooth formed on the inner surface of the distal end of the holder body for permitting one-way rotational movement of the collar relative to the holder body.

The first disc portion may include a lip at a distal end thereof. The holder may further include a compression element such as a coil compression spring positioned about the first disc portion between the lip and the distal end surface of the holder body for biasing the lip away from the distal end surface of the holder body and causing the locking tooth to engage the ratchet tooth and permit one-way rotational movement of the collar relative to the holder body. The compression element preferably provides sufficient outward biasing force such that the needle assembly may be threaded into engagement with the socket without the locking tooth becoming disengaged from the ratchet tooth.

In a further embodiment, the present invention is a medical needle device that includes a needle assembly, a needle holder for holding the needle assembly, and a one-way rotational collar. The needle assembly includes a needle hub supporting a needle cannula. The needle hub has a proximal end and a distal end. The needle holder has a proximal end and a distal end. The distal end of the needle holder defines an opening communicating with the interior of the needle holder. The one-way rotatable collar is in rotational communication with the opening in the holder, and defines a needle assembly receiving socket for connecting the needle assembly to the needle holder. The proximal end of the needle hub is received in the socket. The collar is configured to co-act with the interior of the needle holder such that the collar and needle assembly may rotate in only one direction relative to the needle holder.

The proximal end of the needle hub may be externally threaded and the socket may be internally threaded such that the needle assembly is held in the socket by a threaded connection.

A first end of the needle cannula may be supported by the distal end of the needle hub and project outward from the holder for insertion into the body of a patient. A second end of the needle cannula may be supported by the proximal end of the needle hub and extend into the interior of the holder for connection to a bodily fluid collection tube. An elastomeric sleeve may cover the second end of the needle.

Alternatively, the needle hub may support a first needle at the proximal end thereof and extending into the interior of the holder for connection to a bodily fluid collection tube, and support a second needle at the distal end thereof for insertion into the body of a patient. In a further embodiment, the needle may be supported by the proximal end of the needle hub and extend into the interior of the holder for connection to a bodily fluid collection tube, with the distal end of the needle hub formed as a male luer.

In a further embodiment, the present invention is a holder assembly for receiving a medical needle supported by a hub and for guiding a collection container into piercable engagement with the needle. The holder assembly includes a hollow body comprising a tubular wall extending along an axis between an open end for receiving a collection container and a partially enclosed end. The hollow body includes at least one tooth extending from the tubular wall. The holder assembly also includes a selectively rotatable needle mount engaged with the partially enclosed end of the body. The rotatable needle mount includes a bore with an internal thread spiraling in a first direction about the axis. The rotatable needle mount further includes at least one tooth for interference engagement with the at least one tooth of the hollow body when the needle mount is rotated in the first direction. The interference engagement causes sufficient resistance for a hub supporting a needle to be threaded with the internal thread of the needle mount. Moreover, the interference engagement is insufficient to cause unthreading of a hub threaded with the internal thread of the needle mount when the needle mount is rotated in a direction opposite the first direction.

The present invention is also directed to a method of using a medical needle device in a blood collection procedure, comprising the steps of: (a) providing a medical needle assembly including an externally threaded needle hub and a needle supported by the hub; (b) providing a holder for the needle assembly including a hollow holder body having an end defining an opening communicating with the interior of the holder, with a one-way rotatable collar located in the opening in the holder body and defining an internally threaded needle hub receiving socket; (c) threading the needle hub into the socket in one rotational direction; and (d) preventing the needle hub from being unthreaded from the socket once fully threaded into the socket in the collar.

A further step may be performed by a locking pawl rotationally engaging a ratchet tooth on the inner wall of the holder; by a locking tooth rotationally engaging a ratchet pawl on the inner wall of the holder body; by a locking pawl rotationally engaging a ratchet pawl on the inner wall of the holder body; or by a locking tooth rotationally engaging a ratchet tooth on the inner wall of the holder body.

Further details and advantages of the present invention will become apparent from the following detailed description read in conjunction with the drawings, wherein like parts are designated with like reference numerals.

DETAILED DESCRIPTION

While the present invention is discussed hereinafter in terms of several embodiments, the present disclosure is to be considered as exemplary of the principles of the invention and is not intended to limit the invention to the embodiments illustrated. Various modifications may be made to the present invention by those skilled in the art without departing from the scope and spirit of the present invention. The scope of the present invention is defined by the appended claims and their equivalents.

In the following description and accompanying drawings, the terms "proximal" and "distal" refer to the forward or needle side and rearward or holder side of the device, respectively. These designations will become apparent from the following detailed description.

Figure 1:
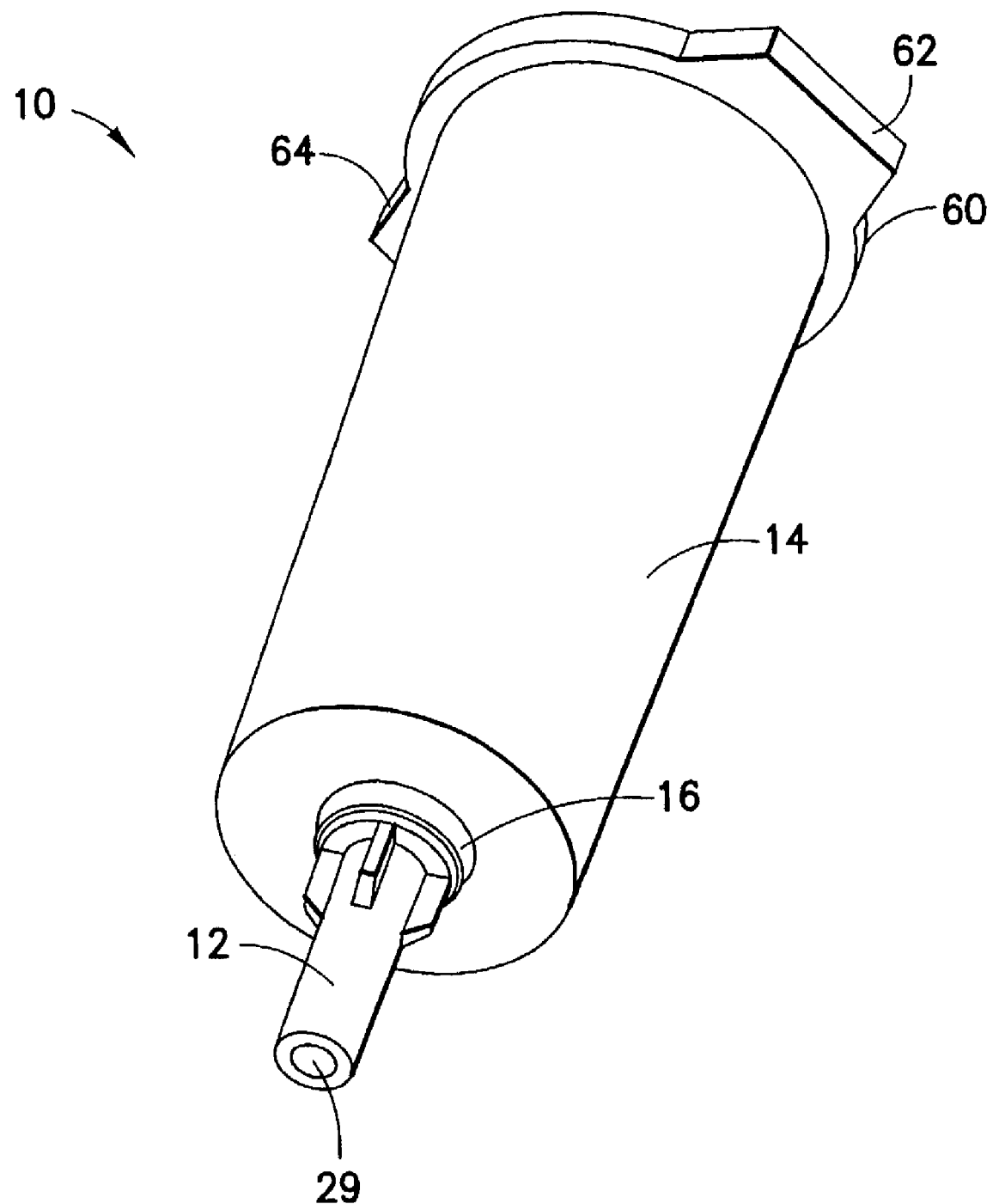
FIG. 1 is a perspective view of a medical needle device in accordance with the present invention.
Figure 2:
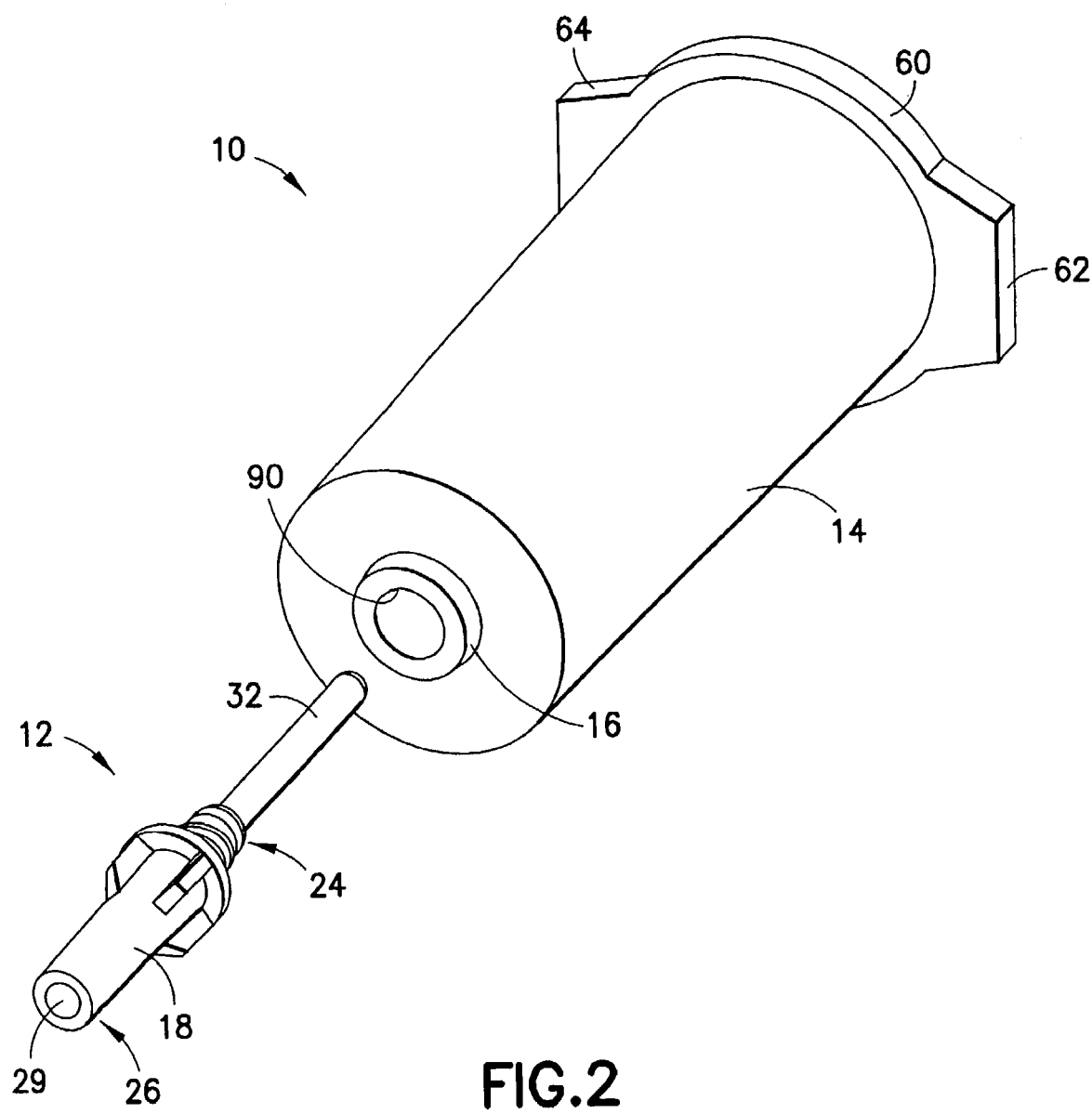
FIG. 2 is an exploded perspective view of the medical needle device of FIG. 1.
Figure 3:
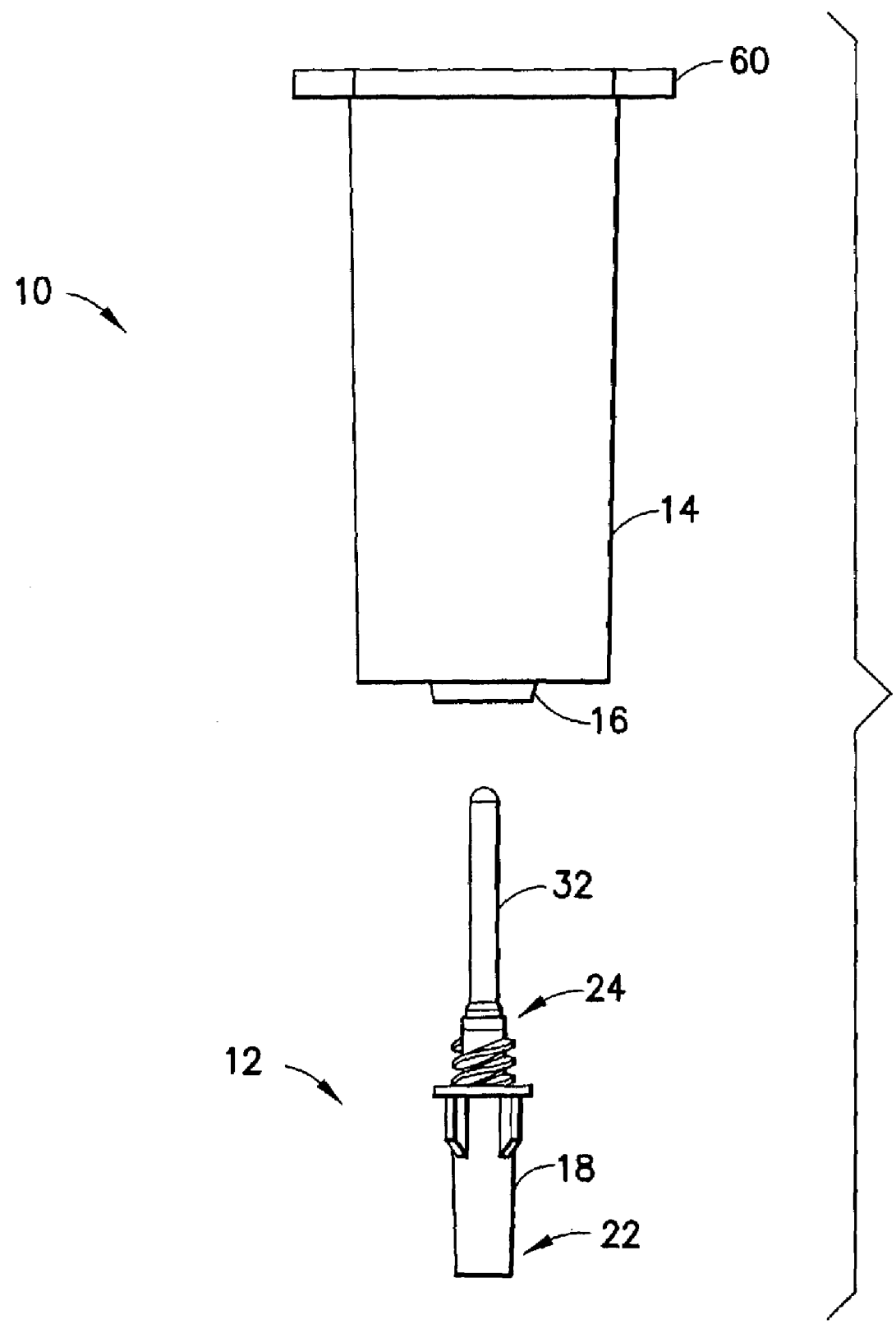
FIG. 3 is an exploded side view of the medical needle device of FIG. 1.
Figure 4:
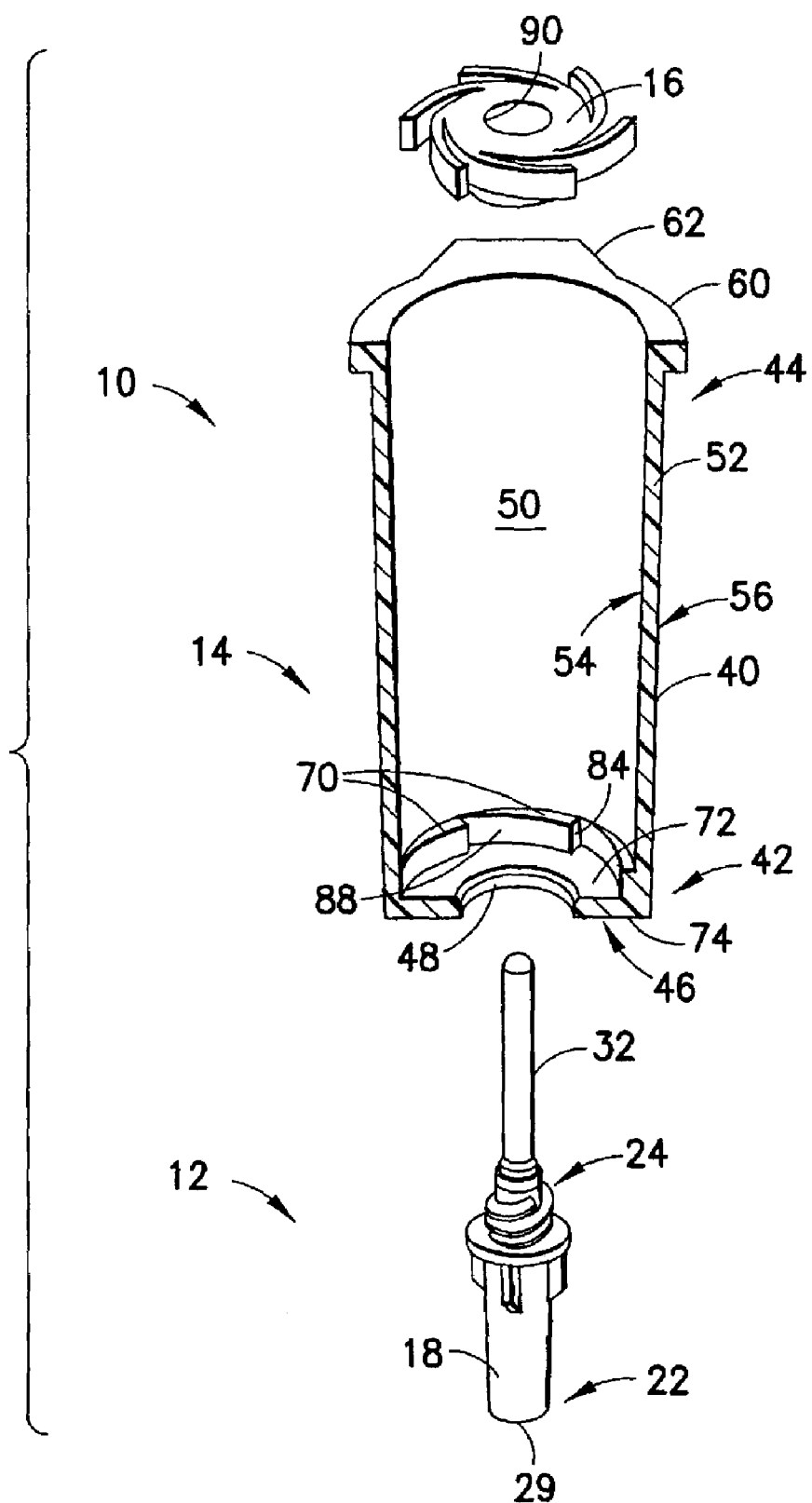
FIG. 4 in an exploded perspective view of the medical needle device of FIG. 1 with a holder of the device shown in cross section.
Figure 5:
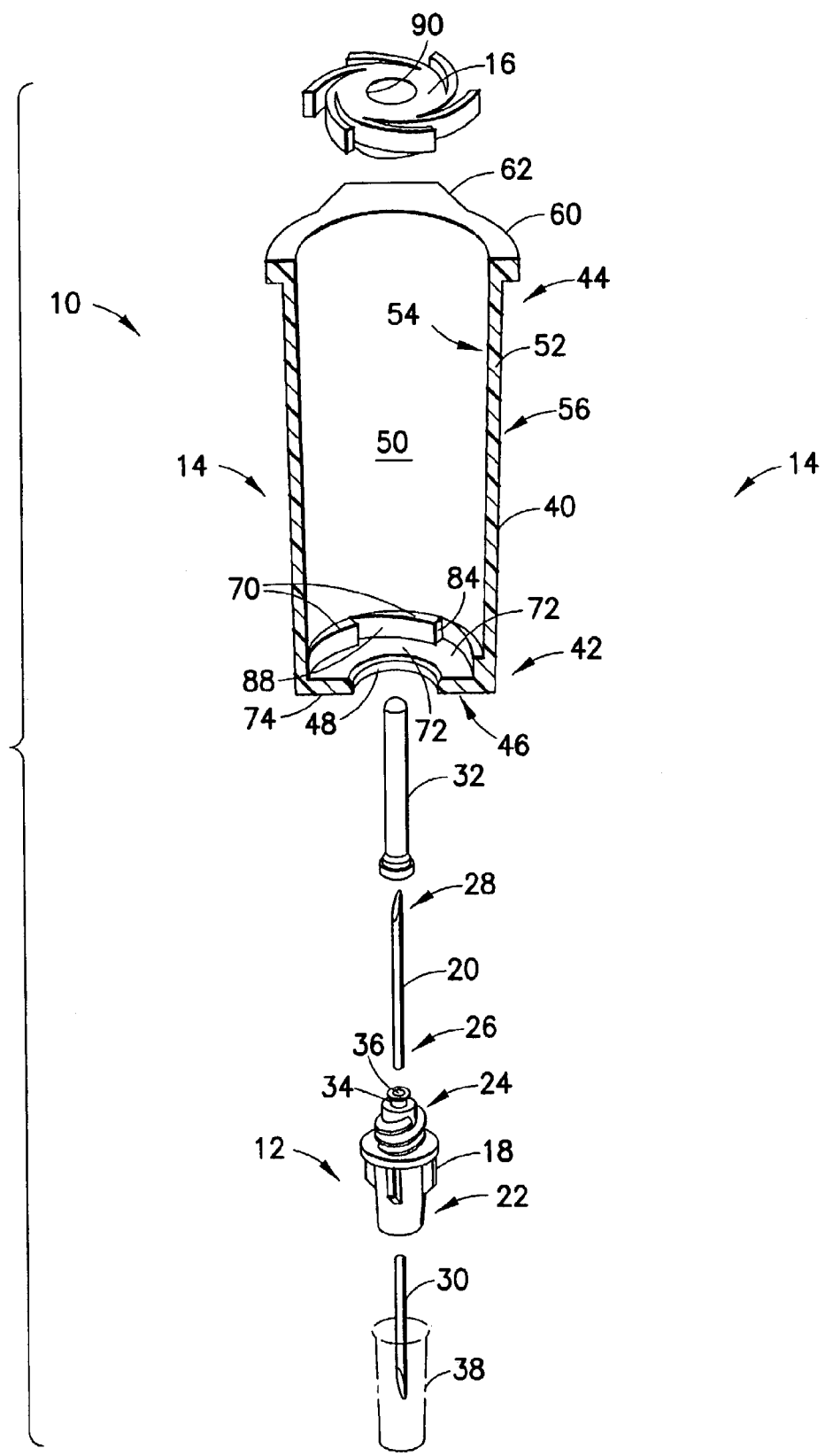
FIG. 5 is an exploded cross sectional view of the medical needle device of FIG. 4, with a needle assembly of the device shown in exploded form.

Referring generally to FIG. 1, a medical needle device 10 in accordance with the present invention is generally shown. The medical needle device 10 is generally intended for use in phlebotomy (i.e. blood collection) procedures and is designed to prevent tampering by a user of the medical needle device 10.

Referring to FIGS. 1–11, a first embodiment of the medical needle device 10 will now be discussed. The principle of operation of the medical needle device 10 of FIGS. 1–11 is illustrative of all the embodiments of the medical needle device 10 to be discussed herein. The medical needle device 10 is generally comprised of a needle assembly 12, a hollow needle assembly holder 14 and a one-way rotatable collar 16 that connects the needle assembly 12 to the holder 14. The assembled medical needle device 10 enables the needle assembly 12 and collar 16 to be rotated in one rotational direction but not in the opposite rotational direction. This prevents inappropriate use by the user of the medical needle device 10. Such inappropriate use includes attempting to remove the needle assembly 12 from the holder 14 at the conclusion of a blood collection procedure. Accordingly, the entire medical needle device 10 is intended to be disposed of at the conclusion of the blood collection or other bodily fluid collection procedure. This reduces the risk of accidental needle stick wounds that may occur if the user attempts to remove the needle assembly 12 from the holder 14.

The needle assembly 12 of the medical needle device 10 includes a needle hub 18 that supports a needle cannula, such as needle 20. The needle 20 may be secured to the needle hub 18 through an adhesive. The adhesive may be any adhesive capable of fixedly attaching or adhering the needle 20 to the needle hub 18, such as a medical grade epoxy or equivalent adhesive. In particular, the needle hub 18 includes a forward or distal end 22 and a rearward or proximal end 24. Likewise, the needle includes a forward or distal end 26 and a rearward or proximal end 28. The distal end 26 of the needle 20 is secured and supported by the proximal end 24 of the needle hub 18. The needle 20 is intended to be disposed within the holder 14 with a non-patient puncture tip at the proximal end 28 thereof for piercing of and insertion into a partially evacuated blood or fluid collection tube (not shown).

The needle hub 18 may be constructed of any material, and is desirably constructed of a molded plastic material. Suitable molded plastics include, but are not limited to, polyethylenes, polypropylenes, polyamides, polyesters, and fluorinated polyethylenes. The proximal end 24 of the needle hub 18 is preferably externally threaded for connection to the collar 16. The distal end 22 of the needle hub 18 is preferably formed as a male luer 29 for mating with a blood collection needle (not shown), which is used to draw blood from the body of a patient. Other arrangements are contemplated for the distal end of the needle hub 18, such as a female luer connection. Alternatively, needle assembly 12 may be formed as a double-ended needle assembly, as will be discussed in more detail with reference to FIGS. 12 and 13 herein.

An elastomeric sleeve 32 preferably covers the needle 20 extending into the holder 14. The needle hub 18 includes a projection 34 with an integrally formed lip 36, which is used to secure the elastomeric sleeve 32 to the proximal end 24 of the needle hub 18. Elastomeric sleeve 32 is deflectable and puncturable by the tip of needle 20 when pressure is inserted therebetween by forcing a piercable closure of a collection tube (not shown) thereagainst, as is common in a blood collection procedure.

The needle assembly 12 is connected to the holder 14 via the one-way rotatable collar 16. The holder 14 includes a holder body 40 having a generally tubular or cylindrical structure extending along an axis. The holder body 40 has a forward or distal end 42 and a rearward or proximal end 44. The distal end 42 includes a distal end face 46 that defines an opening 48. The proximal end 44 of the holder body 40 is open-ended allowing access to the interior 50 of the holder body 40. The interior 50 of the holder body 40 is also cylindrically-shaped. The holder body 40 is formed by a cylindrical wall 52. The cylindrical wall 52 has an inner surface 54 and an outer surface 56.

The proximal end 44 of the holder body 40 forms a flange 60. The flange 60 extends circumferentially around the open proximal end 44 of the holder body 40. The flange 60 may include two oppositely facing projections 62, 64 for grasping by the user of the medical needle device 10. The holder body 40 may be constructed of any material and is desirably constructed of molded plastic material, including all the materials identified previously in connection with the needle hub 18.

In a first embodiment of the medical needle device 10, the wall 52 of the holder body 40 defines a plurality of ratchet teeth 70 on the inner surface 54 of the wall 52. In particular, the ratchet teeth 70 are formed on the inner surface immediately adjacent an inner side 72 of the distal end face 46 of the holder body 40. The ratchet teeth 70 are located in the interior 50 of the holder body 40 to co-act with the collar 16 to allow the one-way rotational motion of the needle assembly 12 and collar 16 with respect to the holder body 40. An outer side 74 of the distal end face 46 of the holder body 40 engages the collar 16, as discussed further herein.

Figure 6:
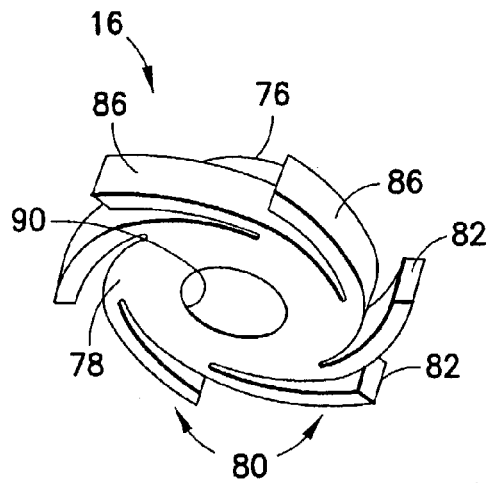
FIG. 6 is a perspective view of a one-way rotational collar used in the medical needle device of FIG. 1.
Figure 7A:
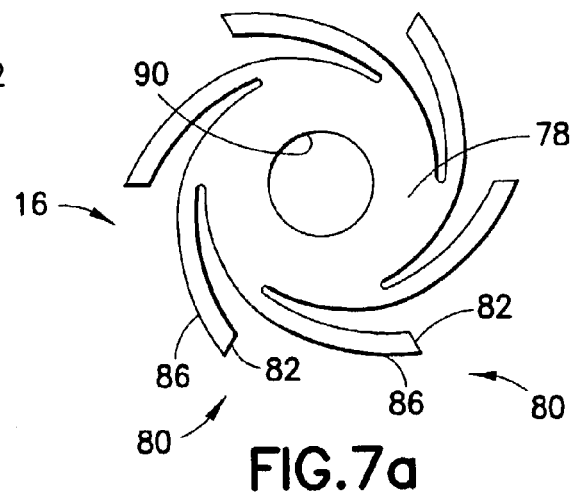
FIGS. 7a, 7b, and 7c show bottom, side, and top views, respectively, of the collar of FIG. 6.
Figure 7B:
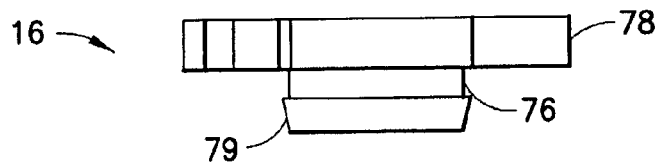
Figure 7C:
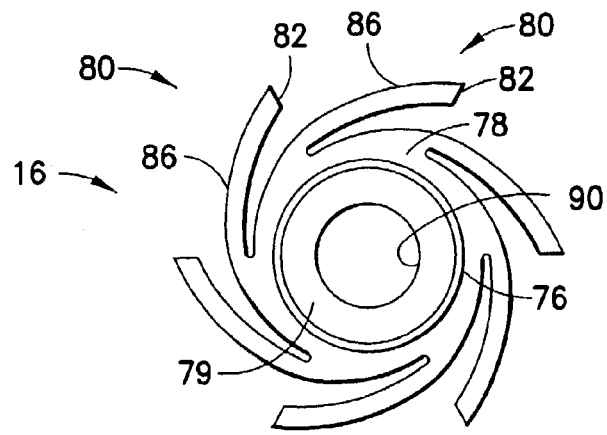
Figure 8:
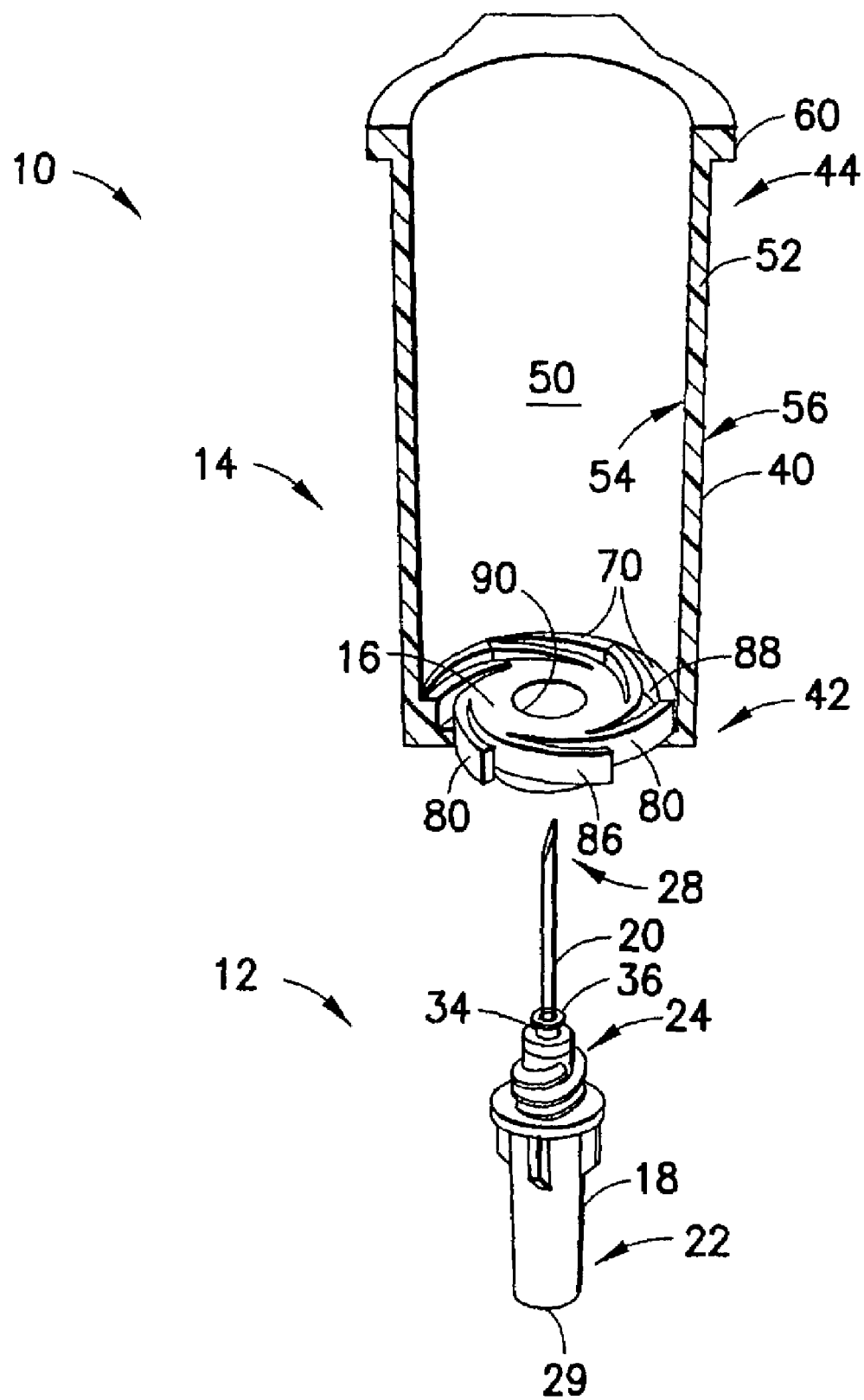
FIG. 8 is an exploded and partial cross-sectional view of the medical needle device of FIG. 1 showing the collar seated in the holder without the sleeve.
Figure 9:
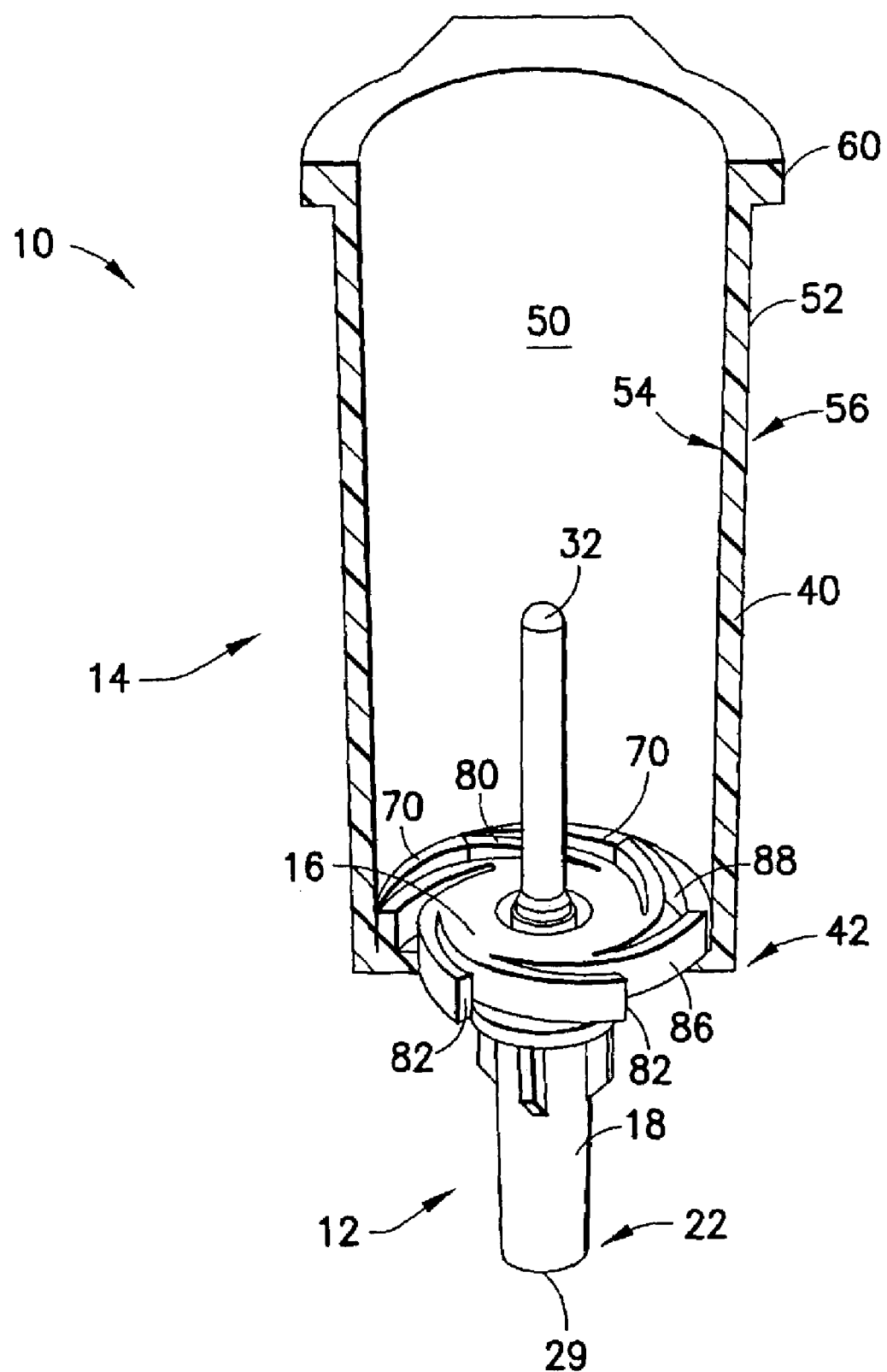
FIG. 9 is a perspective and partial cross-sectional view showing a fully assembled medical needle device in accordance with the first embodiment of the present invention.
Figure 10:
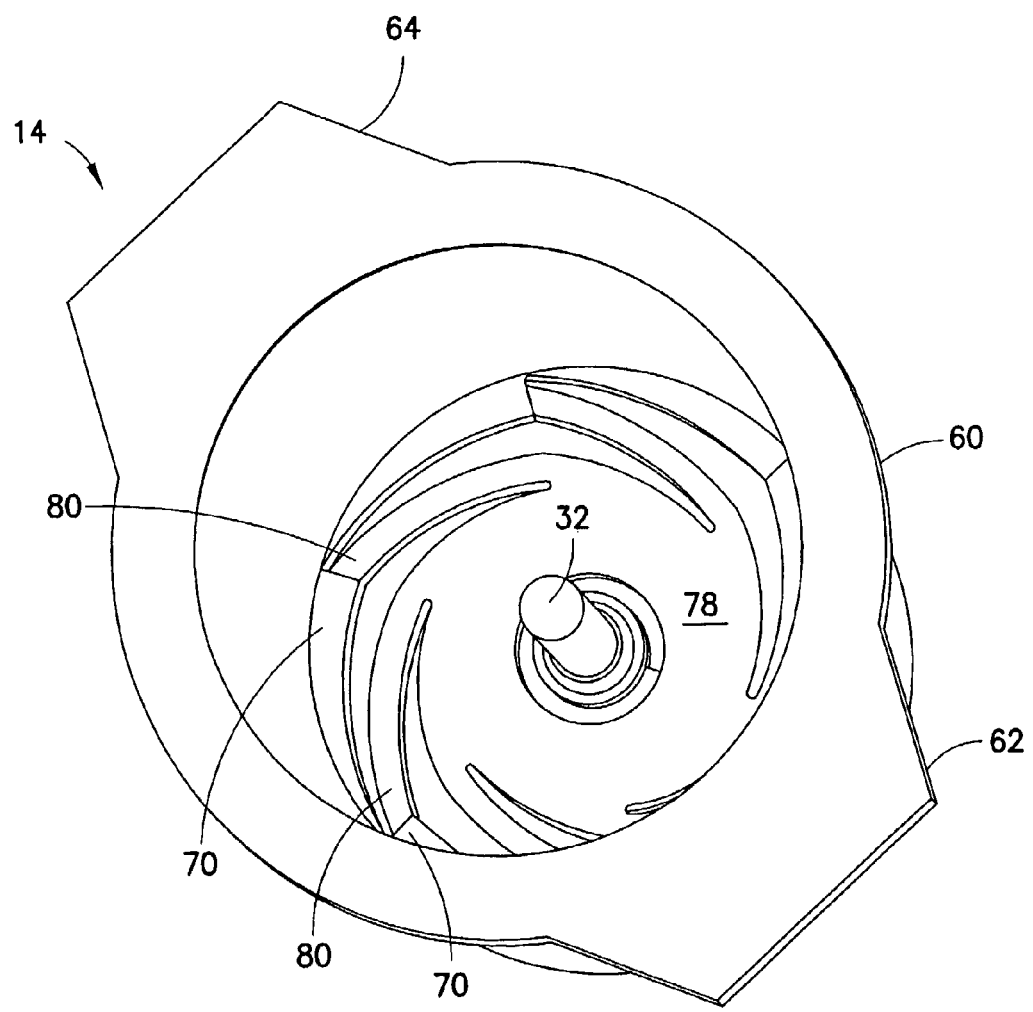
FIG. 10 is a perspective view of a proximal end of the holder of the medical needle device of FIG. 9.
Figure 11:
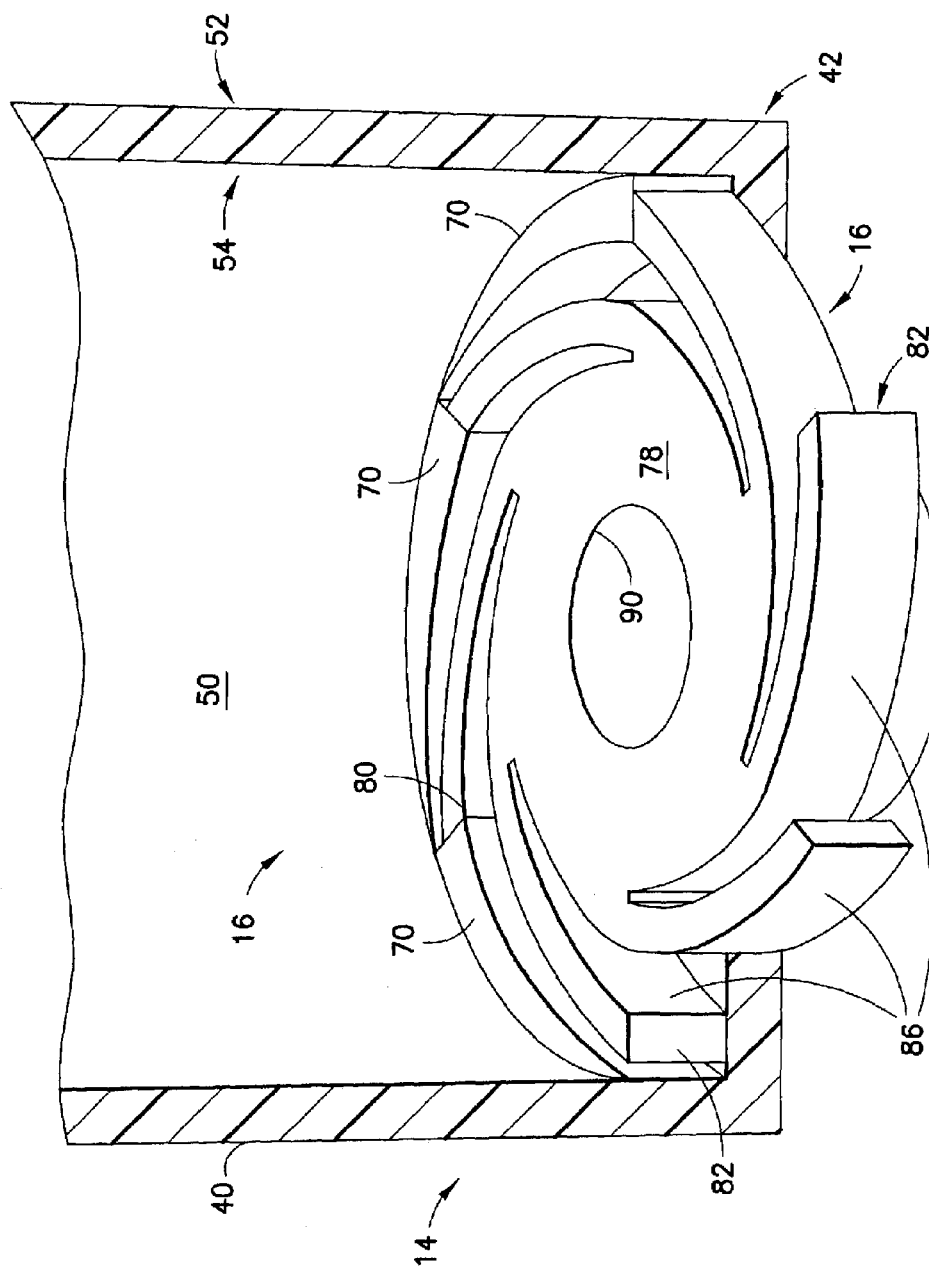
FIG. 11 is a close-up view of the collar shown co-acting with the holder of the medical needle device.

Referring now, in particular, to FIGS. 6 and 7, the one-way rotatable collar 16 will now be discussed. The collar 16 acts as a needle mount for supporting needle assembly 12. The collar 16 is generally defined by a first disc portion 76 and a second, larger diameter second disc portion 78, which are preferably integrally molded as a one-piece unit of molded plastic material. The collar 16 is seated in the opening 48 defined in the distal end face 46 of the holder body 40. In particular, the first disc portion 76 is rotatably received in the opening 48. The collar 16 is maintained in the opening 48 by an integrally formed lip 79. The second disc portion 78 is located entirely within the interior 50 of the holder body 40 as shown, for example, in FIGS. 8–11. The collar 16 may be made of any of the molded plastic materials discussed previously.

Referring again to FIGS. 1–11, the second disc portion 78 includes a plurality of locking pawls 80, which are preferably integrally formed with the second disc 78 portion. The locking pawls 80 are generally formed as elongated structures, each terminating in a flat end face 82. The locking pawls 80 through their respective flat end faces 82 engage the ratchet teeth 70 formed on the inner surface 54 of the wall 52 of the holder body 40. In particular, the ratchet teeth 70 each include flat end faces 84 that contact or co-act with the flat end faces 82 of the locking pawls 80 to prevent rotation of the needle assembly 12 and 16 with respect to the holder 16. The locking pawls 80 further include outward facing surfaces 86 that slidably contact inward facing surfaces 88 of the ratchet teeth 70. The slidable contact between the outward facing surfaces 86 of the locking pawls 80 and inward facing surfaces 88 of the ratchet teeth 70 permit the one-way rotational movement of the needle assembly 12 and collar 16 relative to the holder 14. For example, a clockwise rotational movement of the collar 16 within the holder body 40 allows the outward facing surfaces 86 of the locking pawls 80 to slidably contact the inner facing surfaces 88 of the ratchet teeth 70 permitting the one-way rotational movement of the collar 16 relative to the holder body 40 without the end faces 82 of the locking pawls 80 engaging the end faces 84 of the ratchet teeth 70. Reversing the rotational direction of the collar 16 (i.e., counterclockwise) causes the end faces 82 of the locking pawls 70 to engage the end faces 84 of the ratchet teeth 70, which prevents rotational motion in this direction.

The collar 16 further defines a bore or opening 90 extending therethrough, and through the first and second disc portions 76, 78. The opening 90 is preferably internally threaded spiraling in a first direction about the axis of the holder body 40 forming a needle hub receiving socket. The threaded proximal end 28 of the hub of the needle hub 18 of the needle assembly 12 is threadably received within the threaded opening 90 in the collar 16. Thus, to assemble the medical needle device 10, the needle hub 18 is threadably engaged with the threaded opening 90 in the collar 16. The threaded connection may be conventional with clockwise rotation of the needle hub 18 threadably engaging the threaded opening 90 in the collar 16. The end faces 82 of the locking pawls 80 simultaneously engage the end faces 84 of the ratchet teeth 70, which allows the needle hub 18 to be seated in the collar 16. As such, when a needle assembly rotates collar 16 in a first direction for threading within the socket, the corresponding surfaces of the locking pawls 80 and the ratchet teeth 70 are in interference engagement. Such interference engagement causes sufficient resistance on the collar 16 to permit needle assembly 12 to be threaded with collar 16. In particular, the interference engagement between the locking pawls 80 and the ratchet teeth 70 is greater than the friction or torque which exists between the external threads on the proximal end 28 of the needle hub 18 and the internal threads within the threaded opening 90 of collar 16. As such, rotating the needle hub 18 within the threaded opening 90 of collar 16 in the direction of the spiraling threads causes the needle hub 18 to be threaded therewith.

Once the needle assembly 12 is threadably engaged within the collar 16, the collar 16 prevents the disengagement of the needle assembly 12 from the collar 16 by the sliding interaction between the outward facing surfaces 86 of the locking pawls 80 and the inner facing surfaces 88 of the ratchet teeth 70. In particular, if the needle hub 18 is rotated in a direction opposite the direction of the spiraling threads in an attempt to unthread the needle hub 18 from the threaded opening 90 of collar 16, particular design and arrangement of the locking pawls 80 and the ratchet teeth 70 will cause the locking pawls 80 to slip over the ratchet teeth 70. As such, the interference engagement between the locking pawls 80 and the ratchet teeth 70 is insufficient to cause the needle hub 18 to become unthreaded from collar 16.

As will be appreciated by those skilled in the art, the standard clockwise and counterclockwise convention described hereinabove may be reversed. This may be accomplished by reversing the directions of the locking pawls 80 and ratchet teeth 70 such that counterclockwise rotation of the needle hub 18 relative to the collar 16 will allow the needle hub 18 to threadably engage the threaded opening 90 in the collar 16, while clockwise rotation of the needle hub 18 will allow the locking pawls 80 to slide over and not engage the ratchet teeth 70 on the inner surface 54 of the wall 52 of the holder body 40.

FIGS. 12–32 depict further embodiments of the present invention that include many components which are substantially identical to the components of FIGS. 1–11. Accordingly, similar components performing similar functions will be numbered identically to those components of FIGS. 1–11, except that a suffix "a" will be used to identify those similar components in FIGS. 12–13; a suffix "b" will be used to identify those similar components in FIGS. 14–19; a suffix "c" will be used to identify those similar components in FIGS. 20–21; a suffix "d" will be used to identify those similar components in FIGS. 22–26; and a suffix "e" will be used to identify those similar components in FIGS. 29–32.

Figure 12:
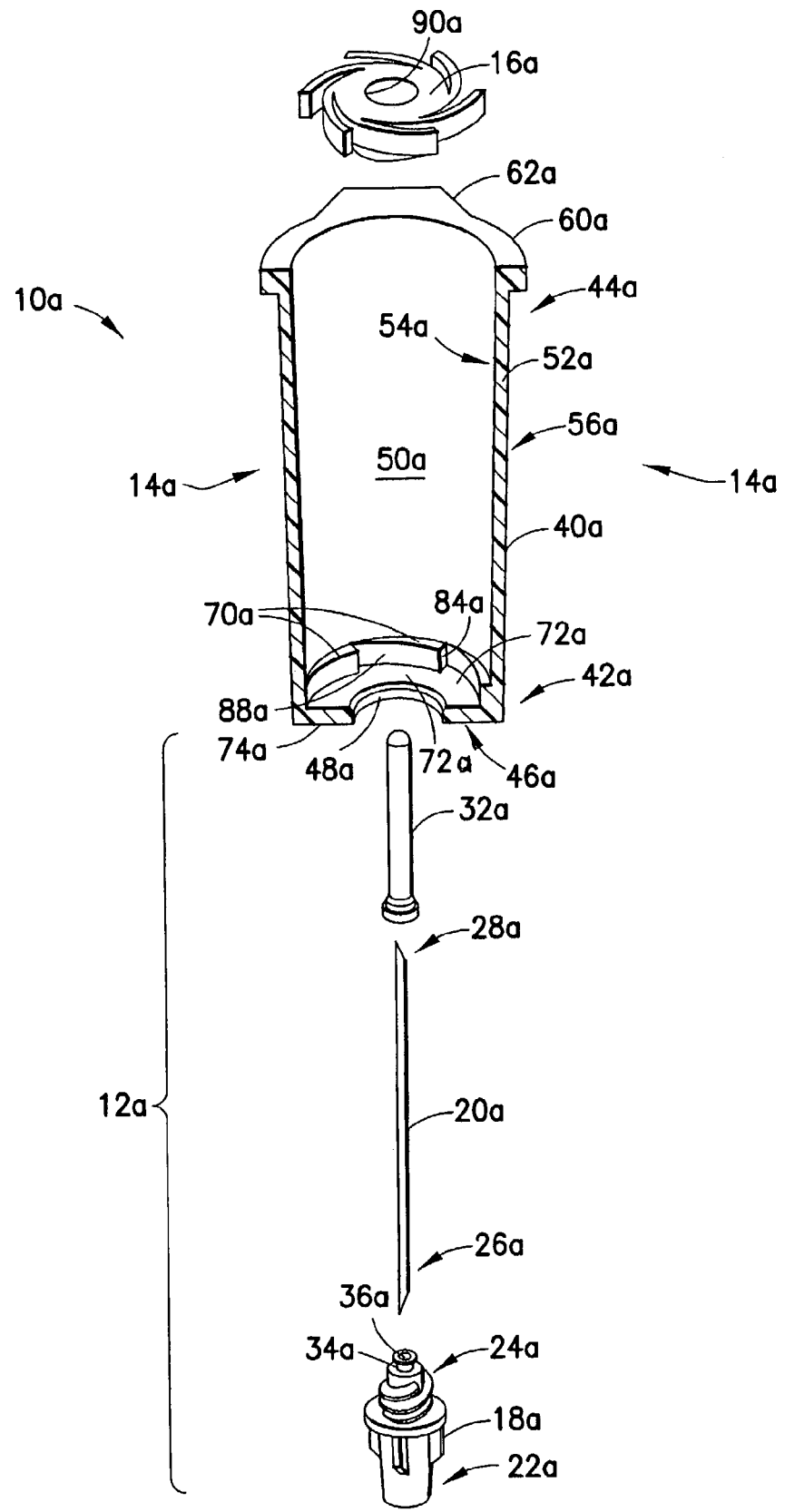
FIG. 12 is an exploded cross-sectional view of a medical device in an alternate embodiment, with the needle assembly shown in exploded form as a double-ended needle assembly.
Figure 13:
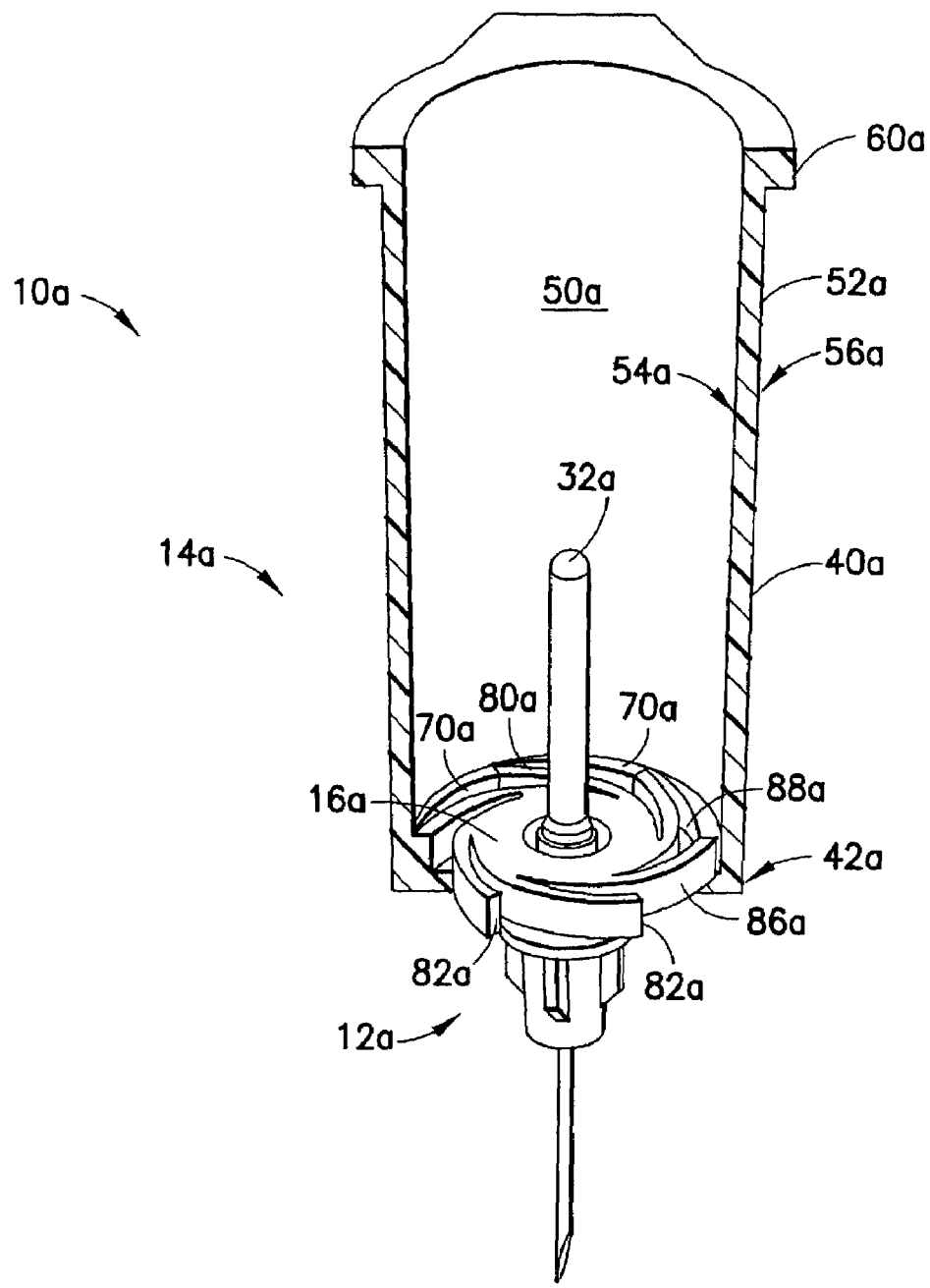
FIG. 13 is a perspective and partial cross-sectional view showing a fully assembled medical needle device of FIG. 12.
Figure 14:
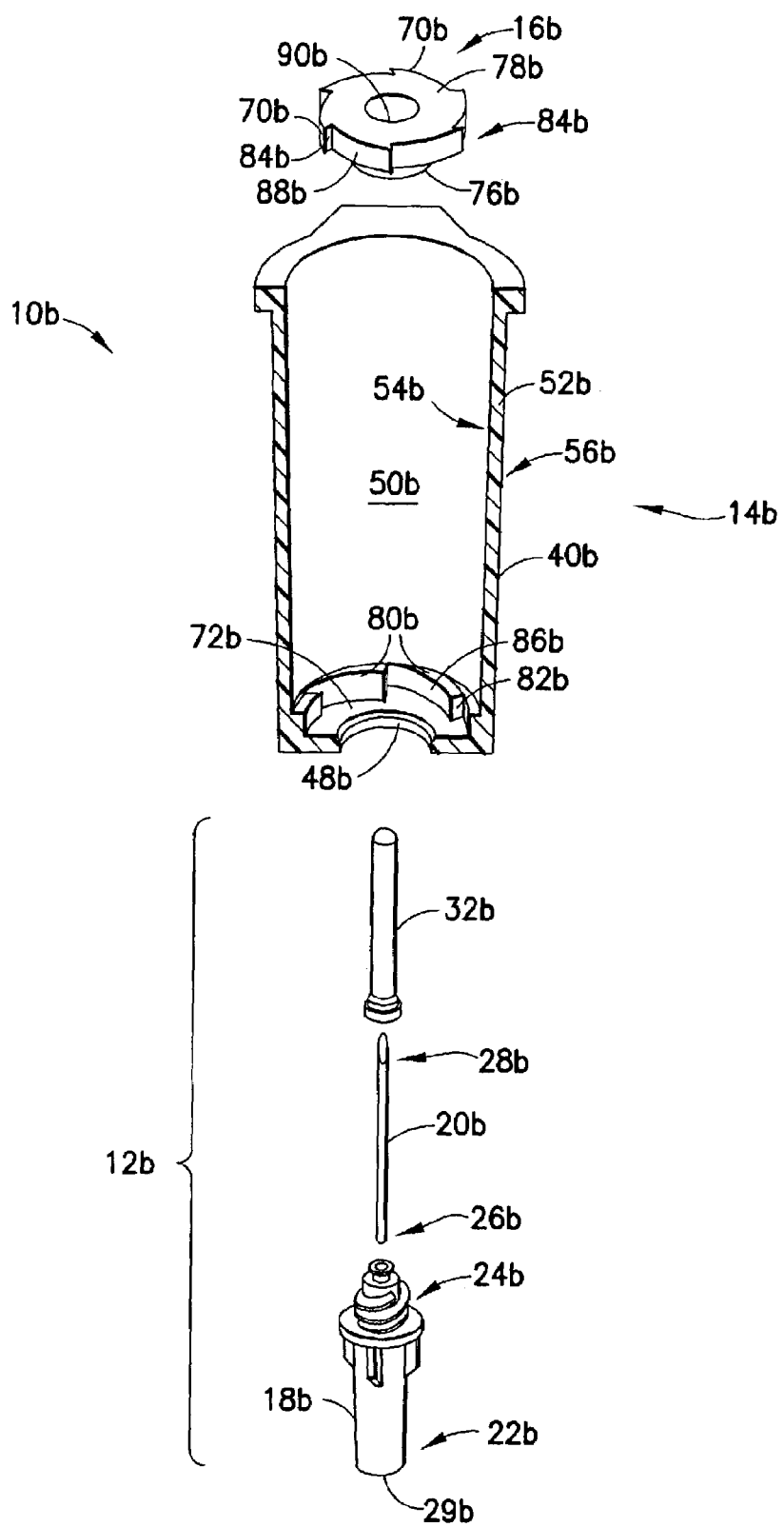
FIG. 14 is an exploded perspective view of a second embodiment of the medical needle device in accordance with the present invention.
Figure 15:
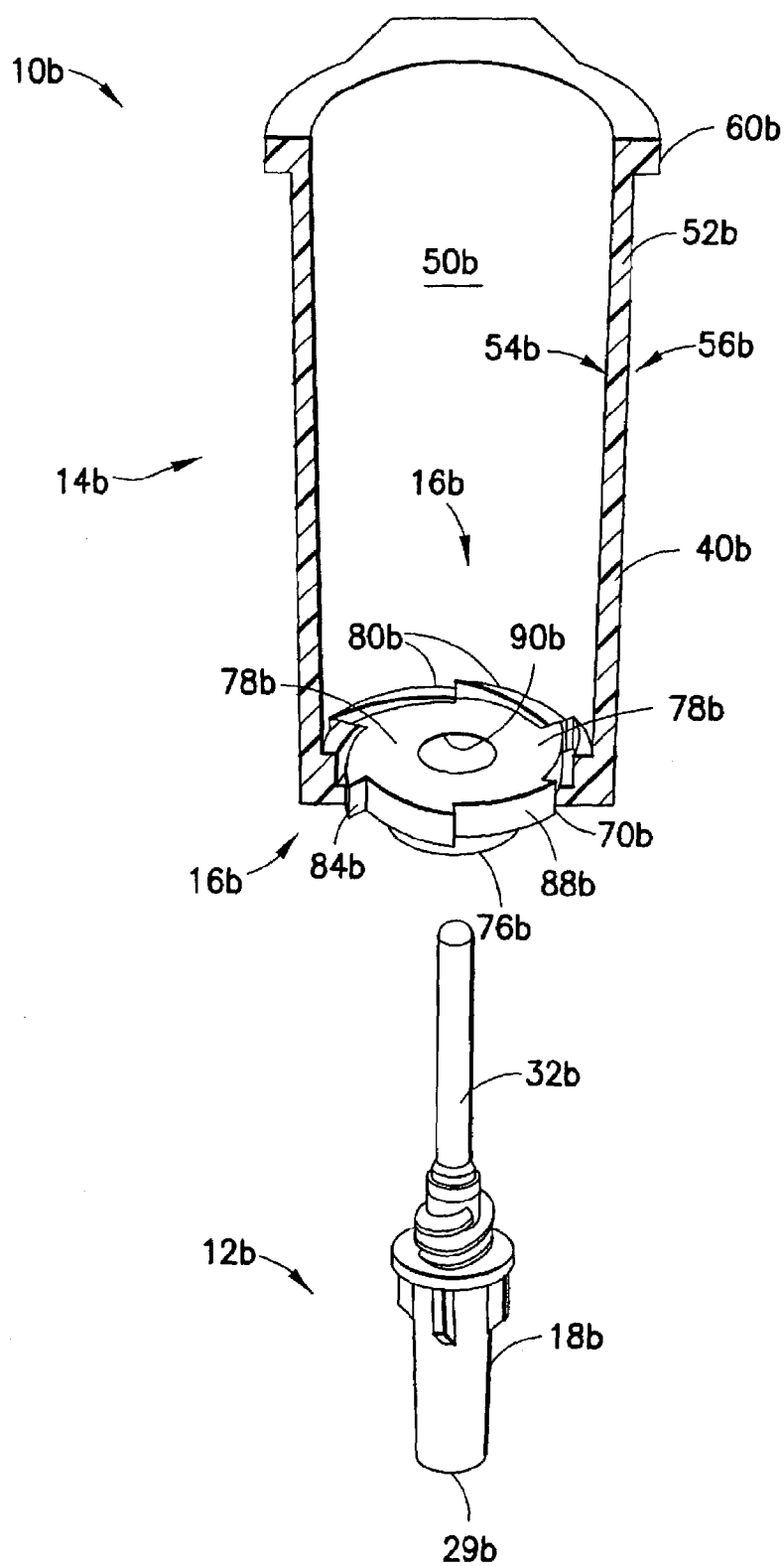
FIG. 15 is an exploded perspective view of the medical needle device of FIG. 14 showing the needle assembly detached from the holder of the device.
Figure 16:
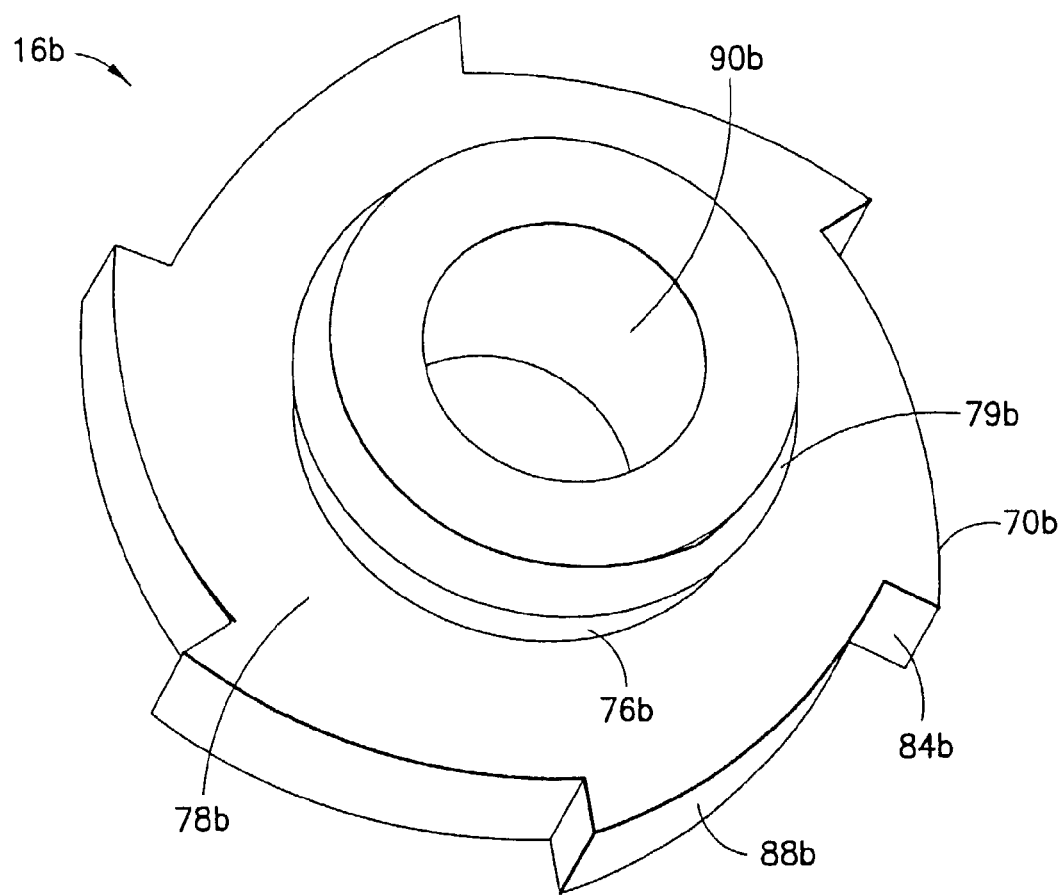
FIG. 16 is a top perspective view of the collar used in the medical needle device of FIG. 14.
Figure 17:
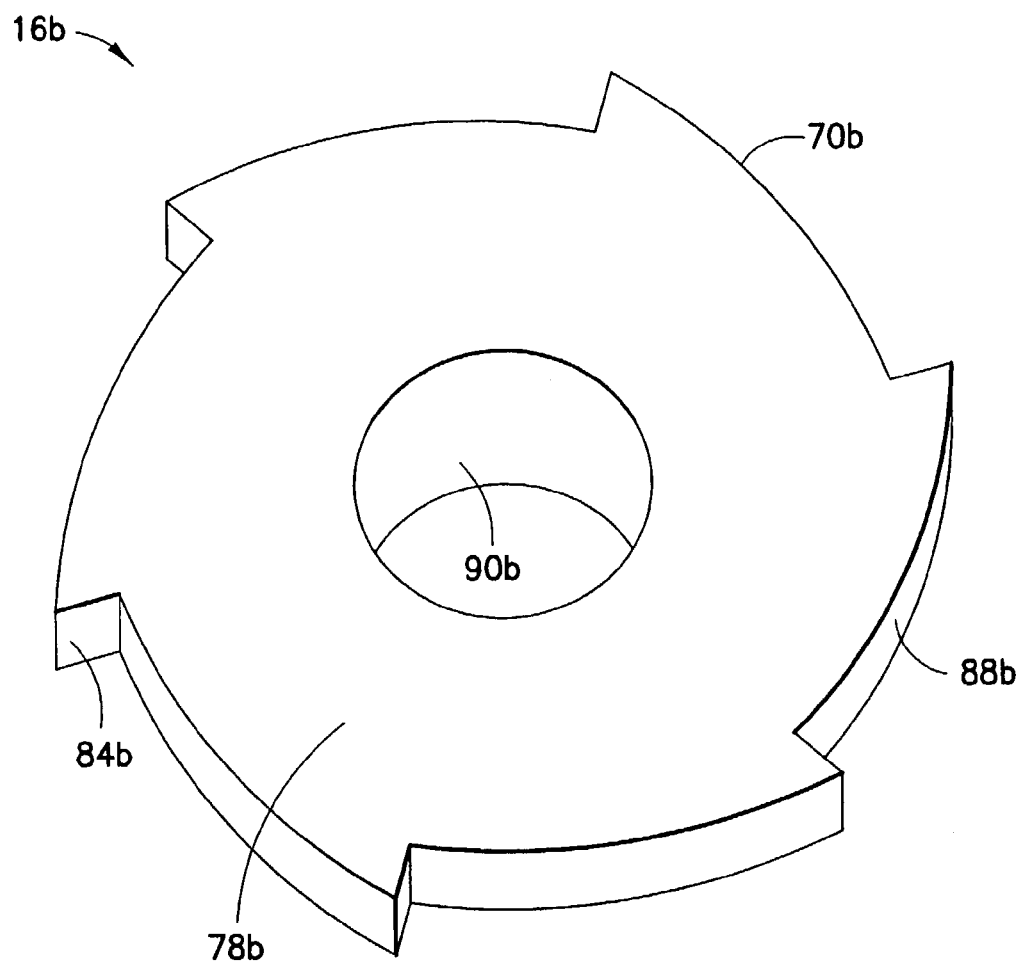
FIG. 17 is a bottom perspective view of the collar used in the medical needle device of FIG. 14.
Figure 18:
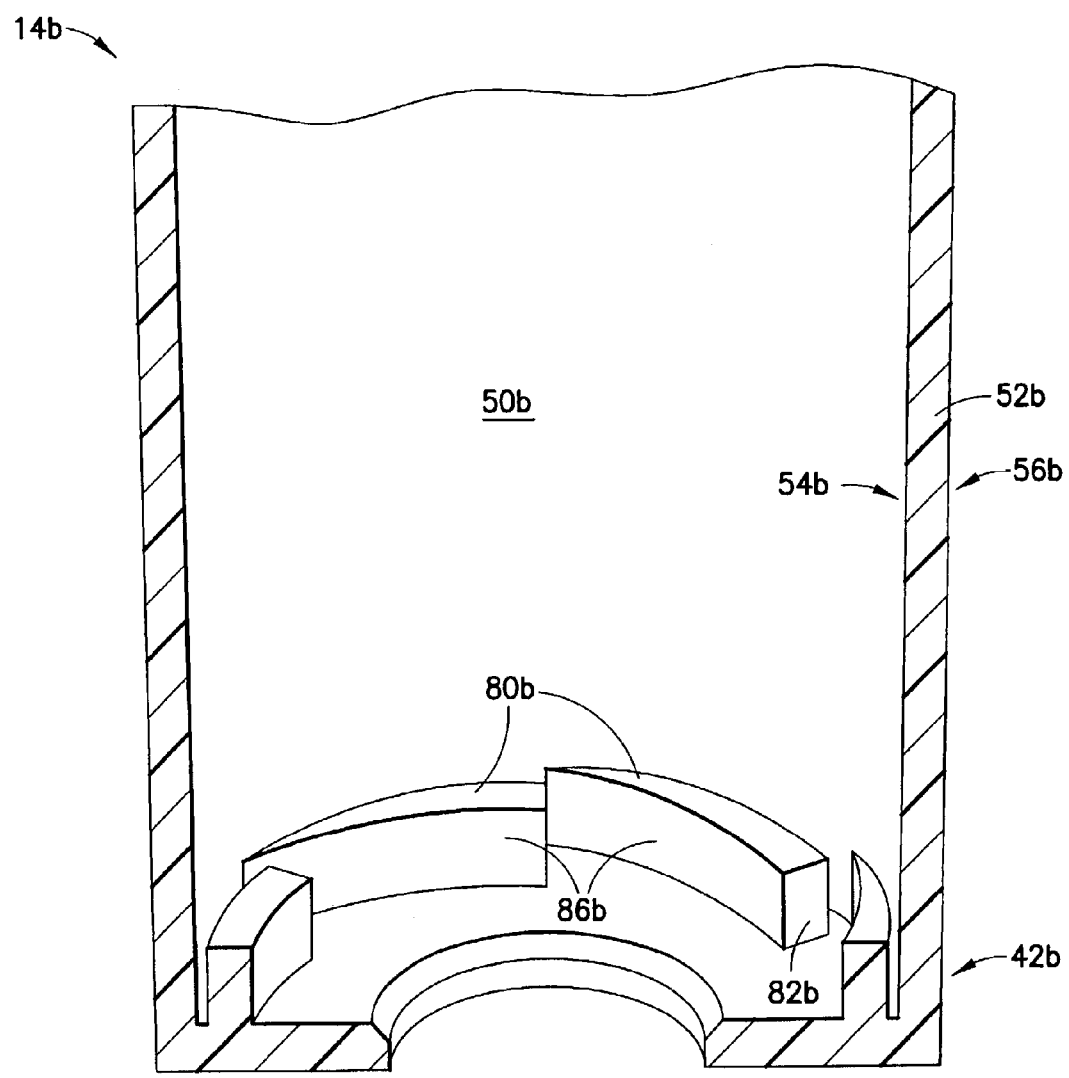
FIG. 18 is a close-up perspective and partial cross-sectional view of a distal end of the holder used in the medical needle device of FIG. 14
Figure 19:
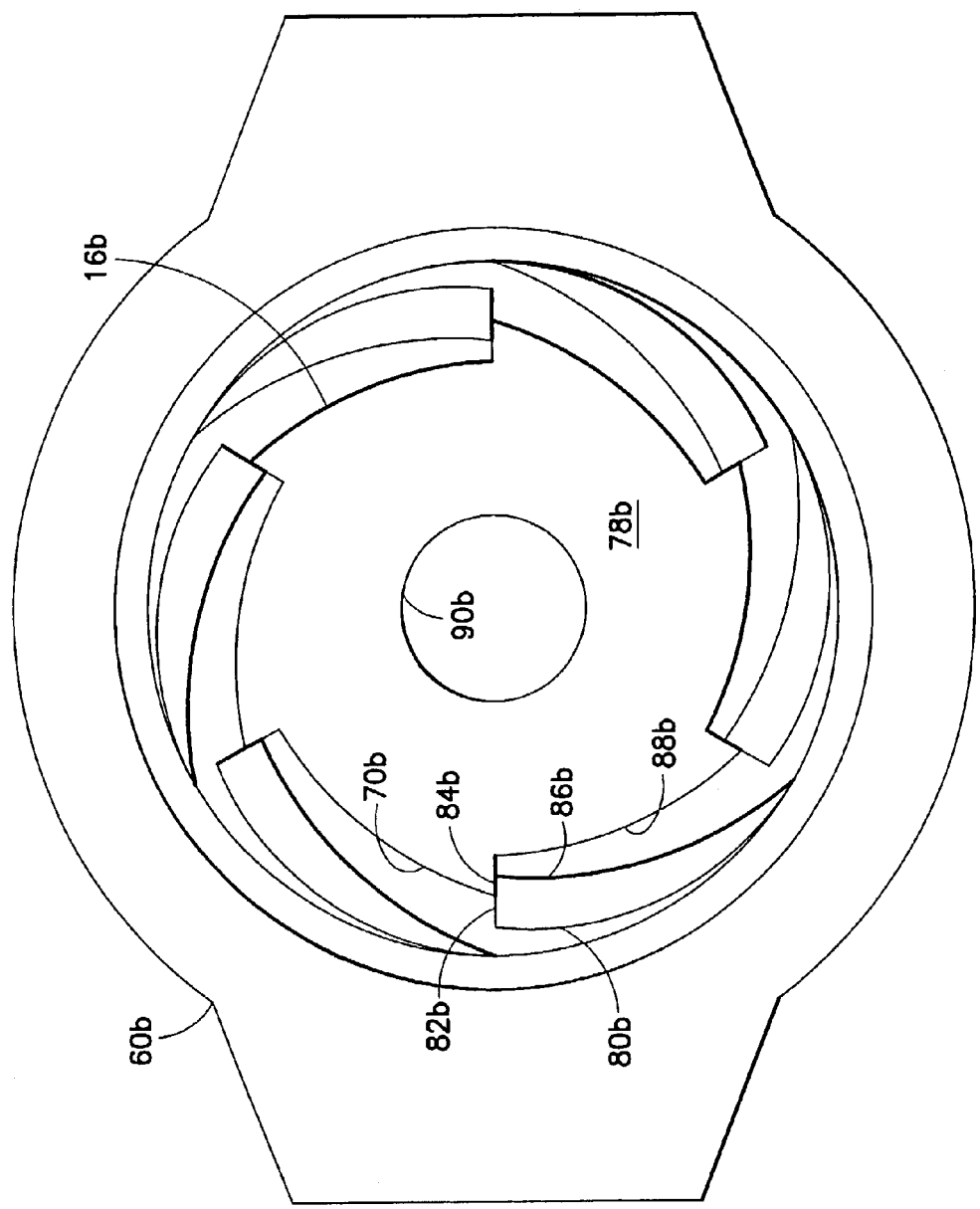
FIG. 19 is a close-up view of the proximal end of the holder used in the medical needle device of FIG. 14.

Referring to FIGS. 12–13, medical needle device 10a is shown with an alternate needle assembly 12a in the form of a double-ended needle assembly, such as is commonly used in phlebotomy procedures. Needle assembly 12a includes needle hub 18a for engagement with needle holder 14a, and a double-ended needle cannula in the form of needle 20a. Proximal end 28a of needle 20a includes a non-patient puncture tip as described above. Distal end 26a of needle 20a includes an intravenous puncture tip at the end thereof, for insertion into a patient during a blood collection procedure. Needle 20a extends through needle hub 18a, with the proximal end 28a of needle 20a extending from proximal end 24a of needle hub 18a, and with distal end 26a of needle 20a extending from distal end 22a of needle hub 20a. Alternatively, needle 20a can be provided with proximal end 28a and distal end 26a as separate members which are separately attached to the respective ends of needle hub 18a.

Referring to FIGS. 14–19, a further embodiment of the medical needle device is shown and designated with reference character 10b. The medical needle device 10b is identical to the medical needle device 10 discussed hereinabove, with the exception that the locations of the locking pawls and ratchet teeth are reversed. Accordingly, the locking pawls 80b are now formed on the inner surface 54b of the wall 52b of the holder body 40b immediately adjacent to the inner side 72b of the distal end face 46b of the holder body 40b. The ratchet teeth 70b are now formed on the second disc portion 78b of the collar 16b. The medical device 10b will operate in an identical manner to the medical needle device 10a discussed previously, with only the locations of the locking pawls 80b and ratchet teeth 70b being reversed.

Figure 20:
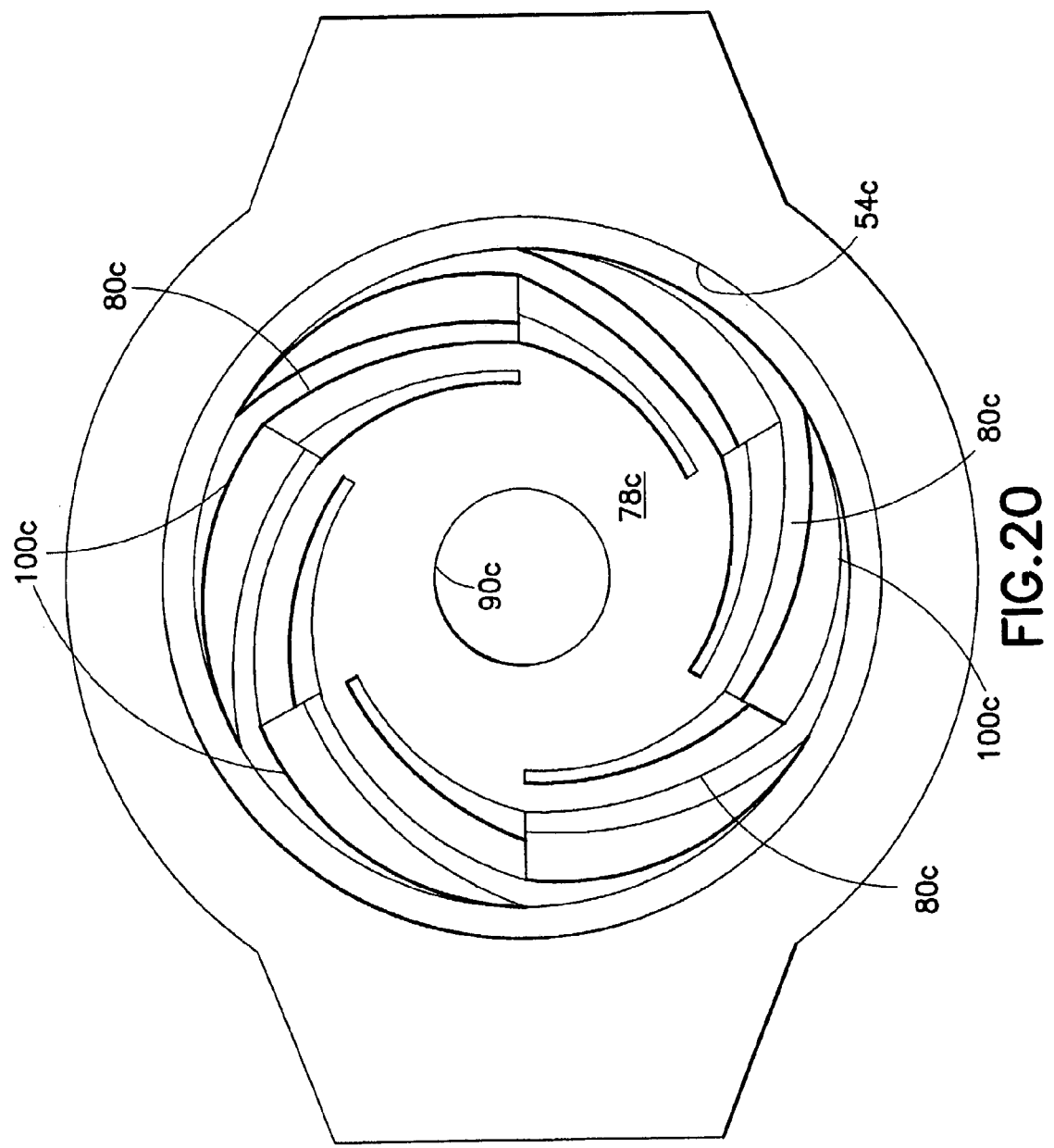
FIG. 20 is a bottom view of the medical needle device in accordance with a third embodiment of the present invention, with the device viewed from the bottom or proximal end of the holder.
Figure 21:
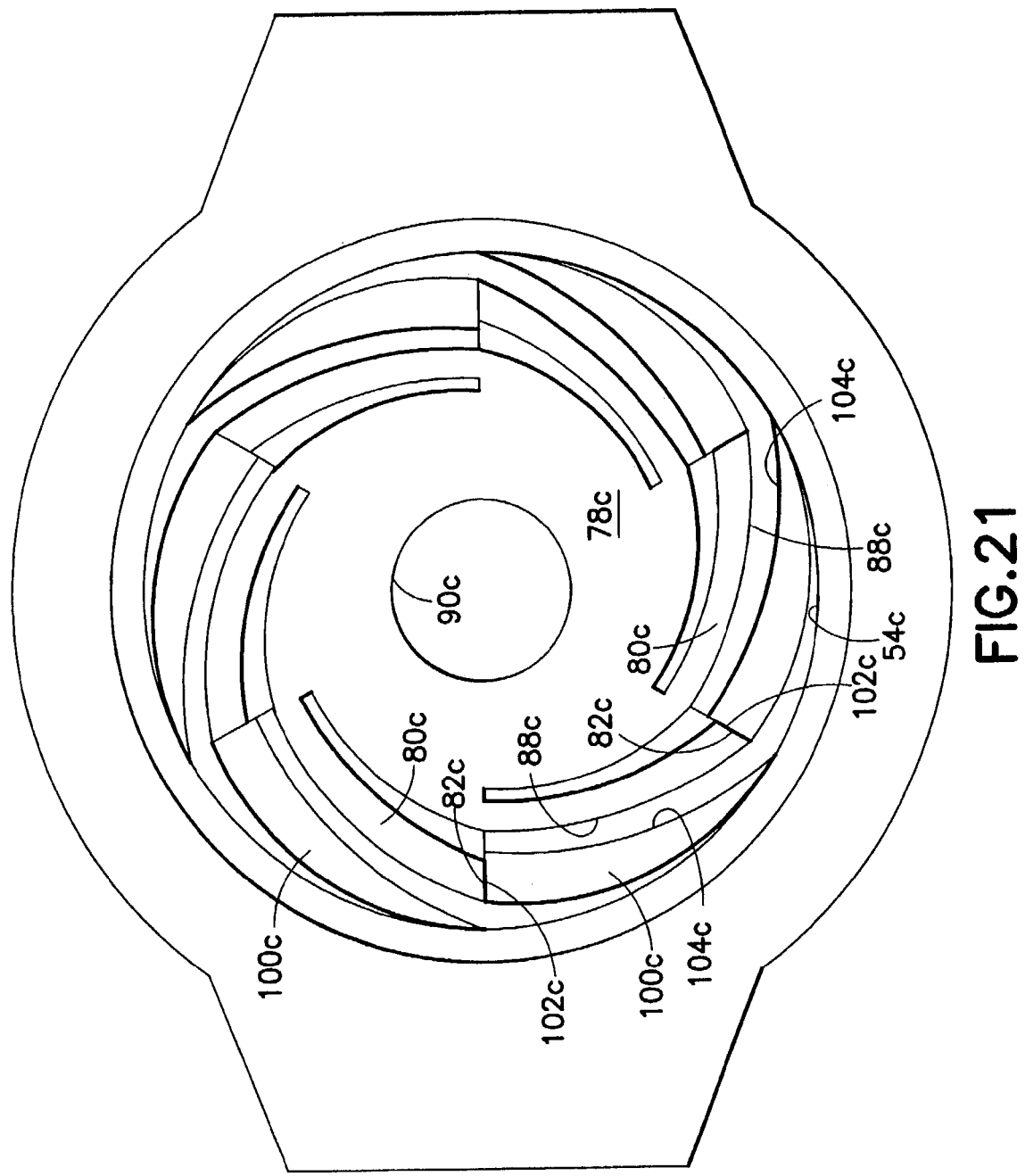
FIG. 21 is an enlarged view of the view shown in FIG. 20.
Figure 22:
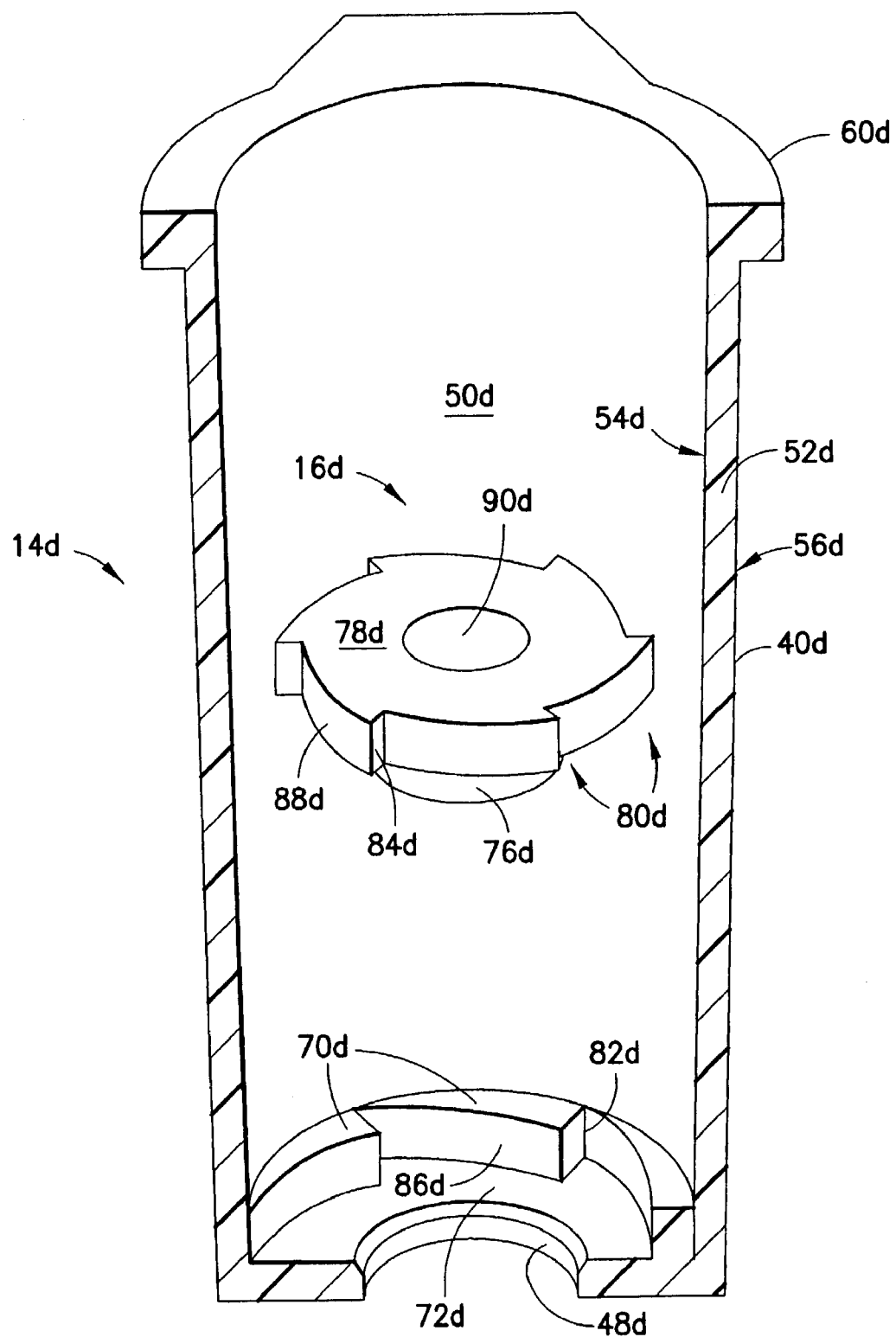
FIG. 22 is a perspective, partially exploded, and partial cross-sectional view of the holder and collar used in the medical needle device in accordance with a fourth embodiment of the present invention.
Figure 23:
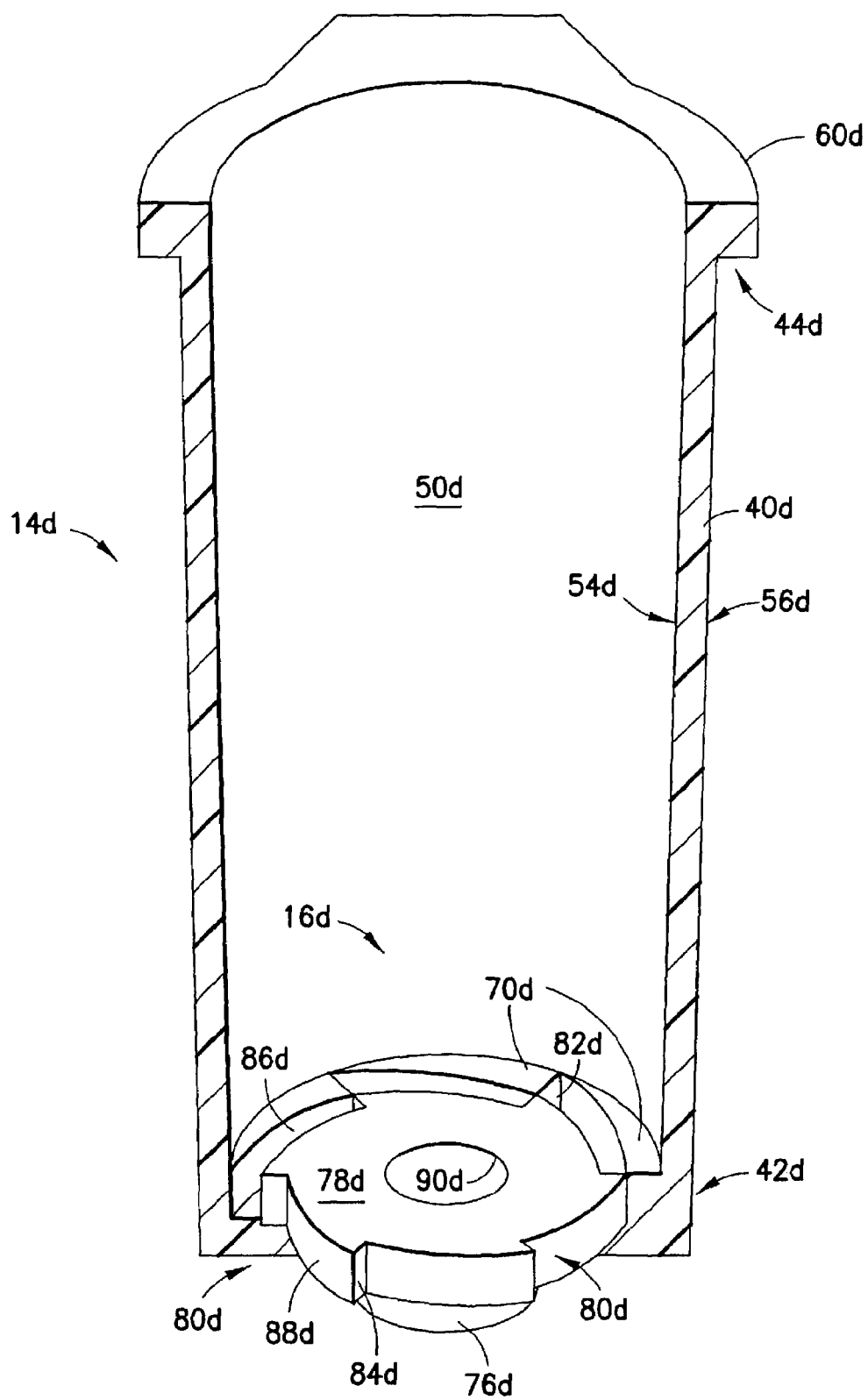
FIG. 23 shows the collar in a seated, assembled position within the holder of FIG. 22.
Figure 24:
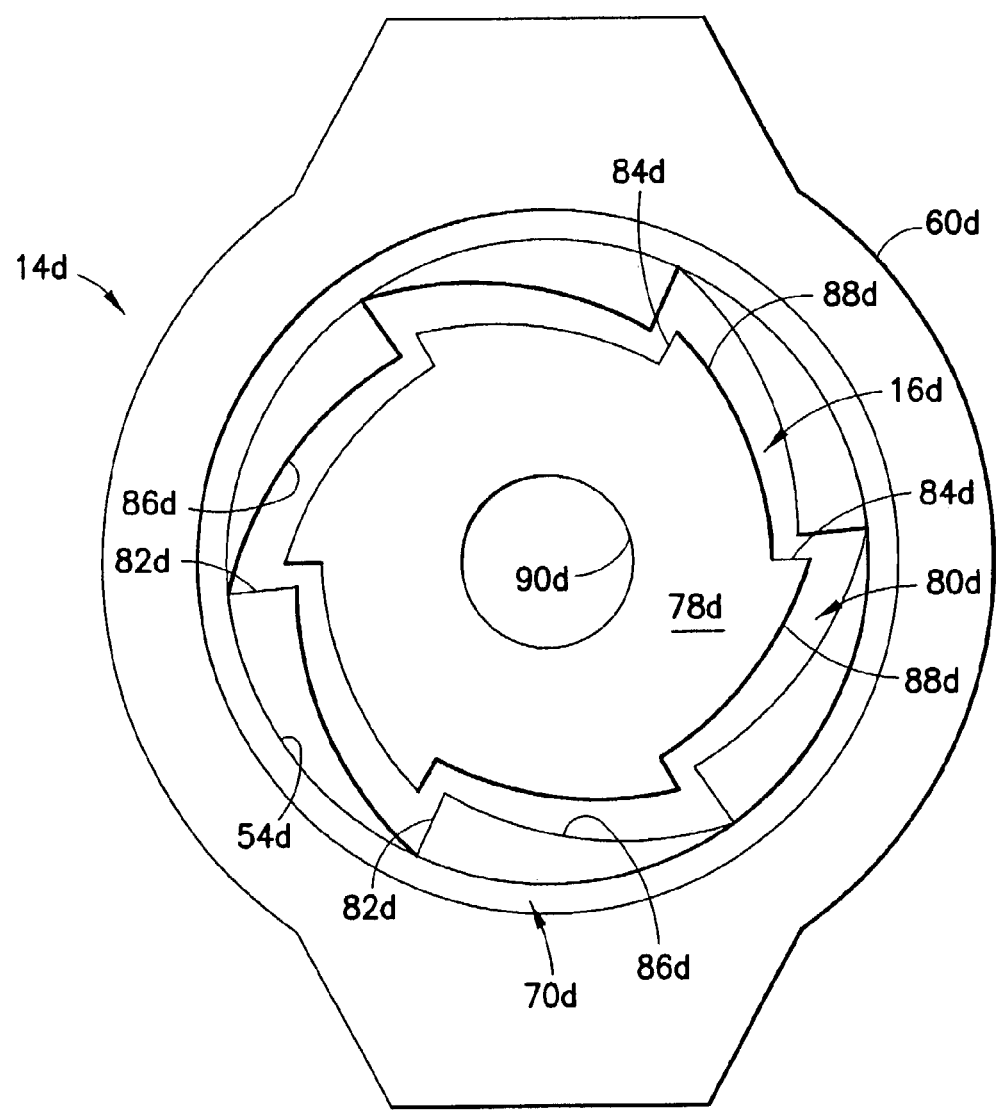
FIG. 24 is a close-up bottom or proximal view of the holder of FIGS. 22 and 23.
Figure 25:
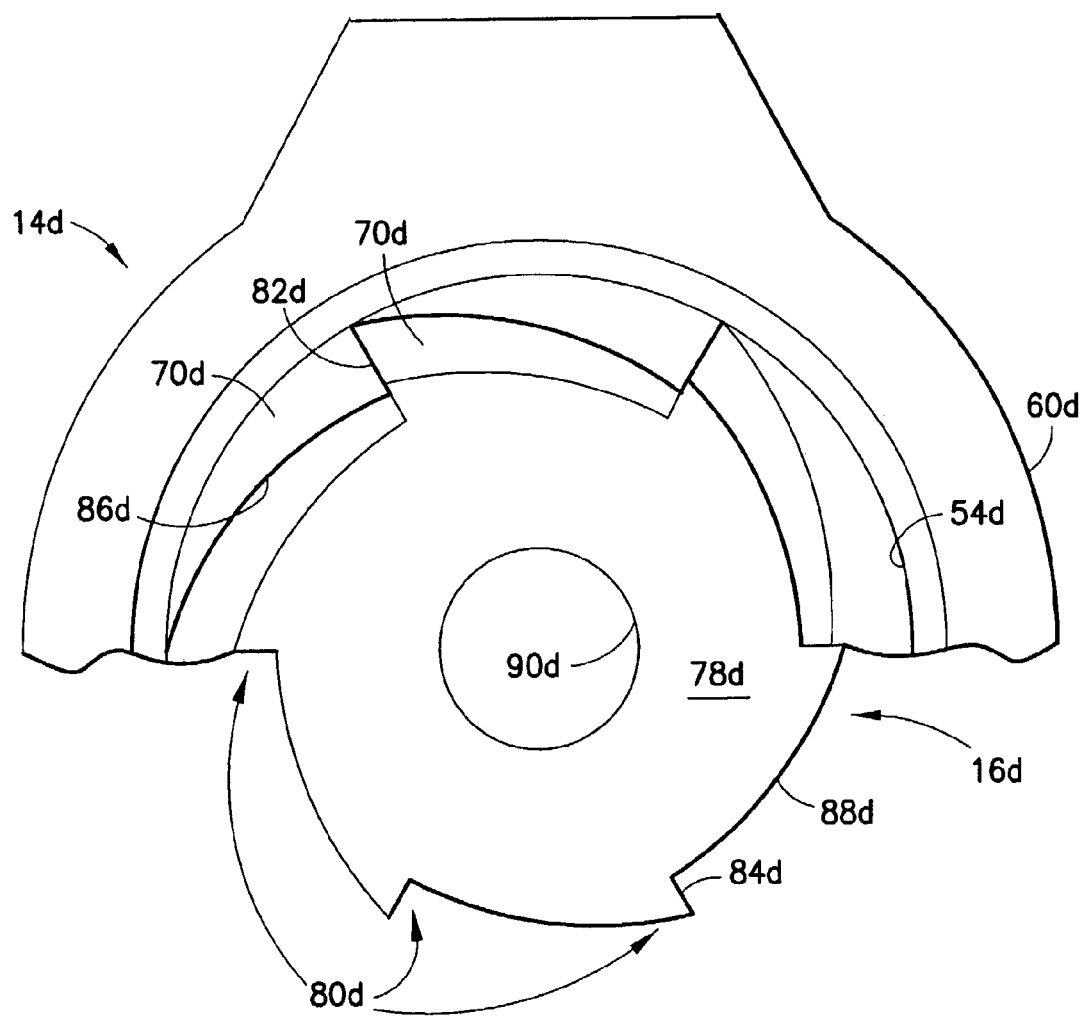
FIG. 25 is a close-up detail view showing the engagement of the rotational collar with the holder of FIG. 22.
Figure 26:
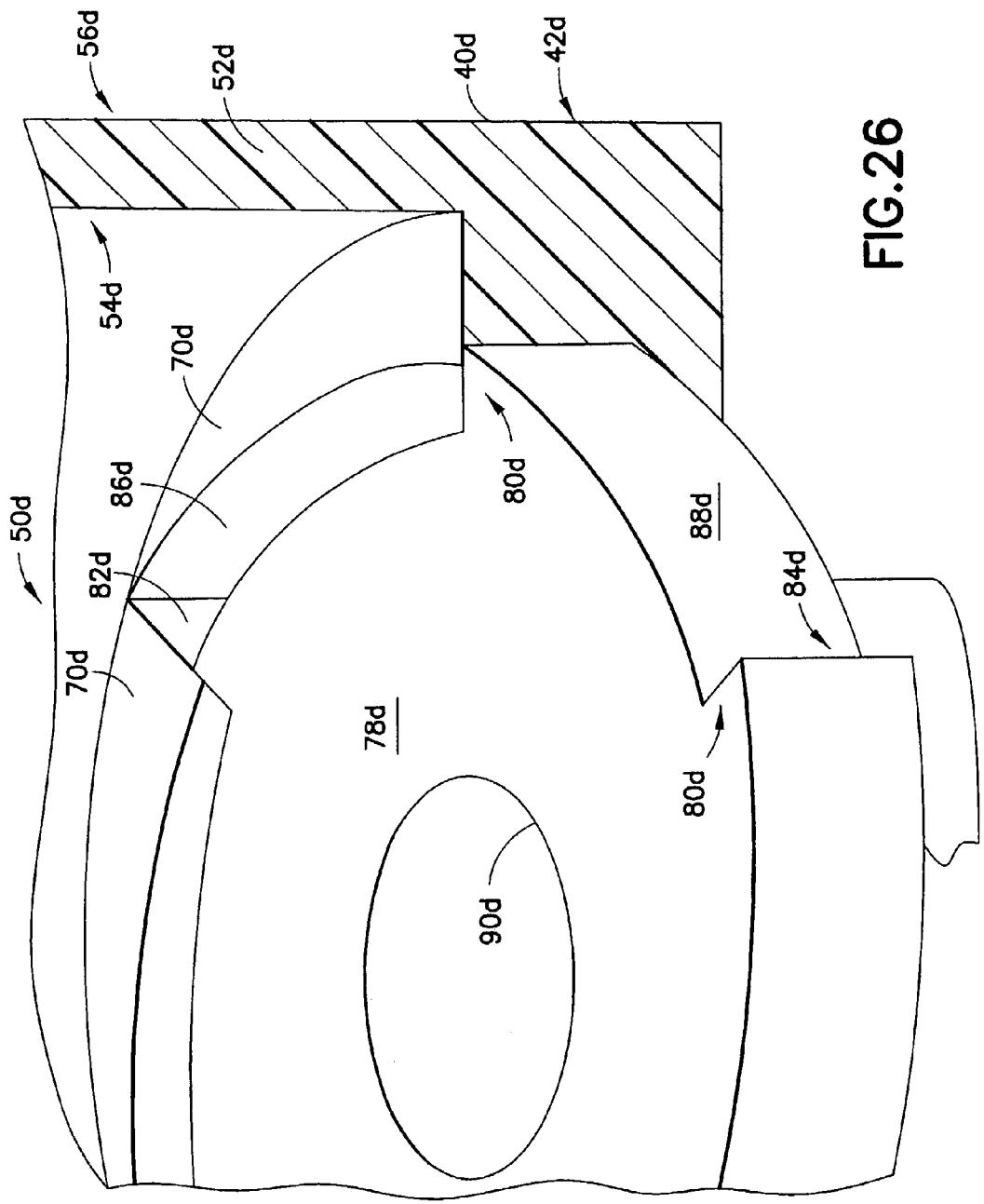
FIG. 26 is a close-up perspective and partial cross-sectional view of the engagement between the rotational collar and holder of FIG. 25.
Figure 27:
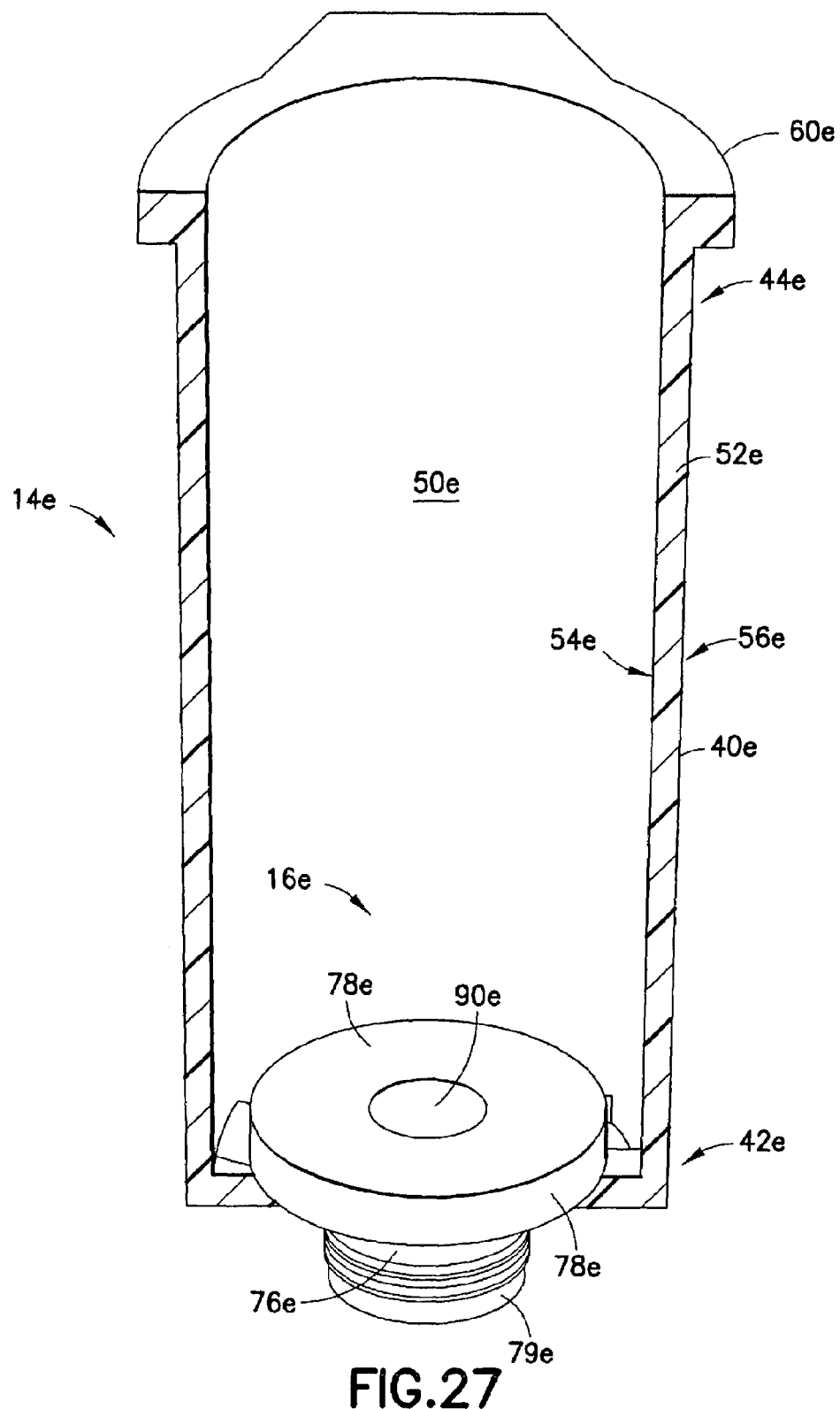
FIG. 27 is a perspective and partial cross sectional view of a holder and rotational collar used in the medical needle device in accordance with a fifth embodiment of the present invention.
Figure 28:
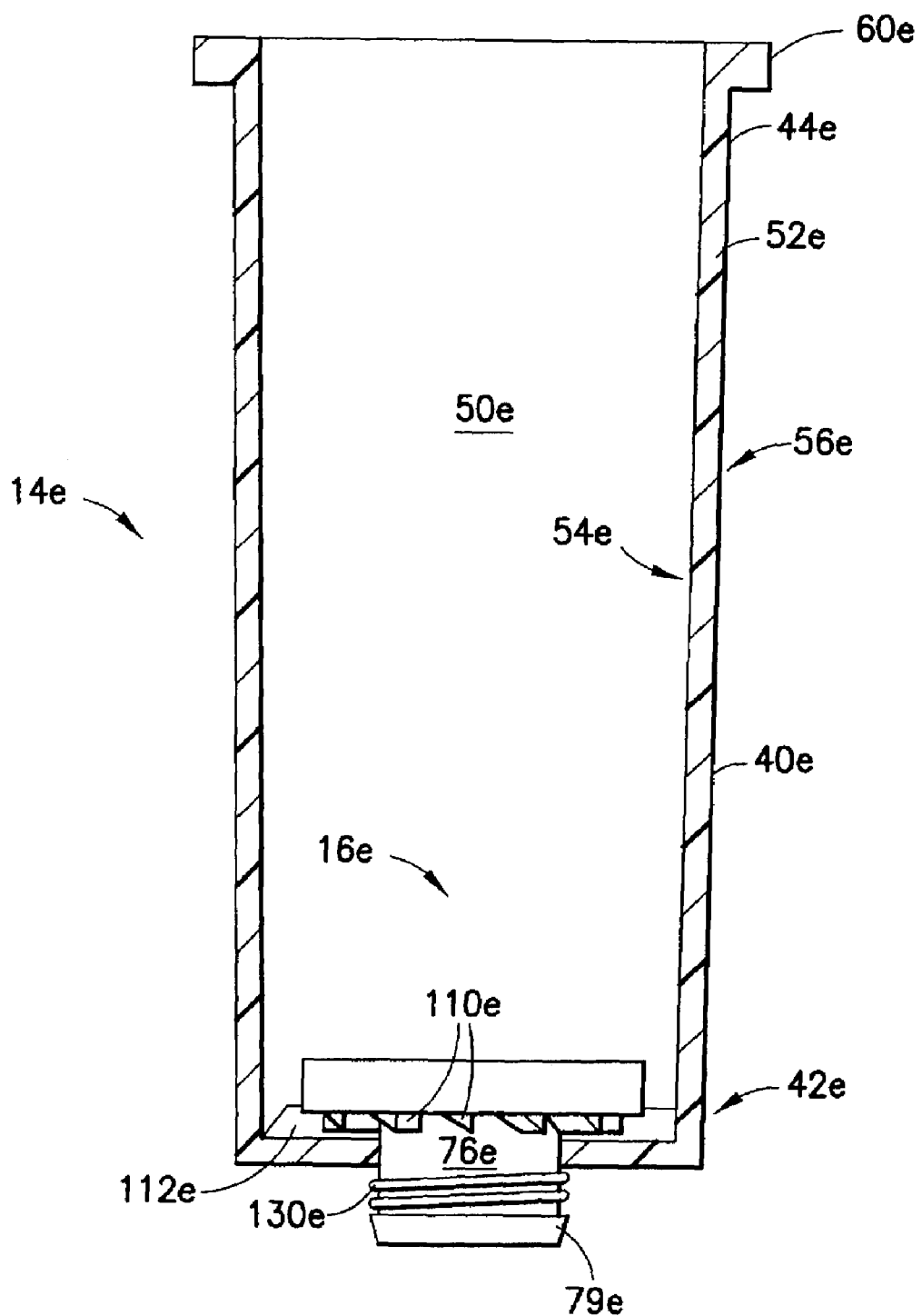
FIG. 28 is a side and partial cross sectional view of the holder and collar of FIG. 27.
Figure 29:
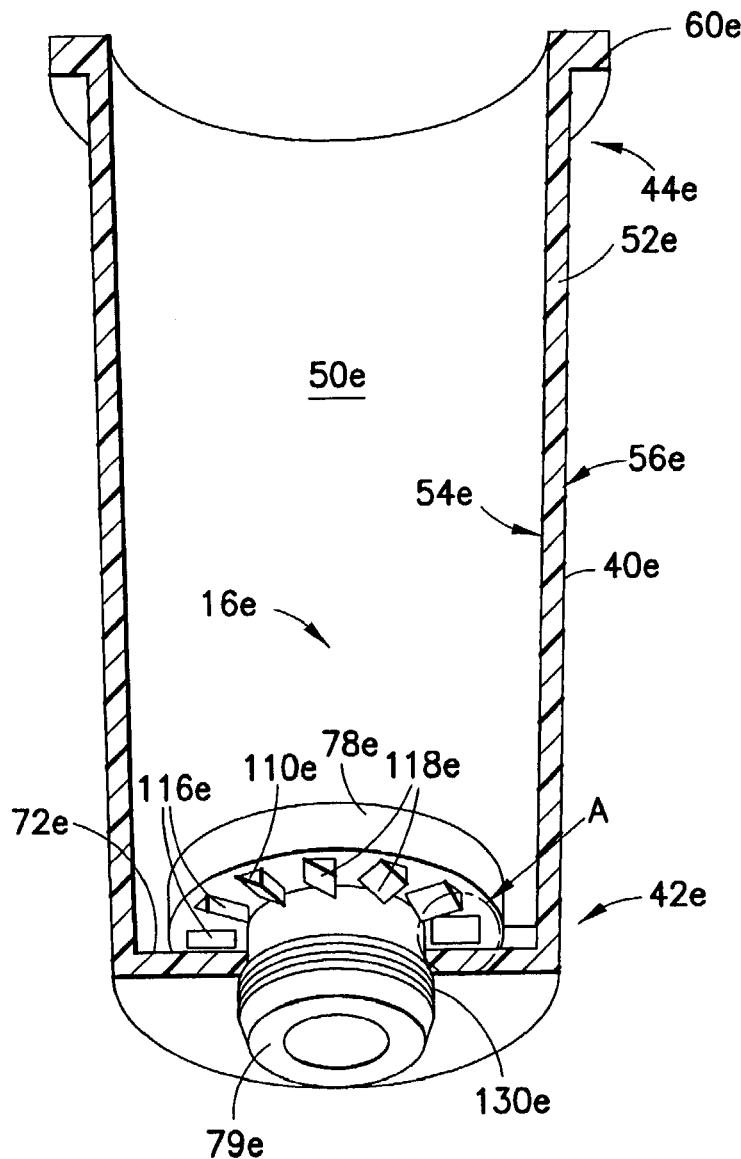
FIG. 29 is a bottom perspective and partial cross sectional view of the holder and rotational collar of FIG. 27.
Figure 30:
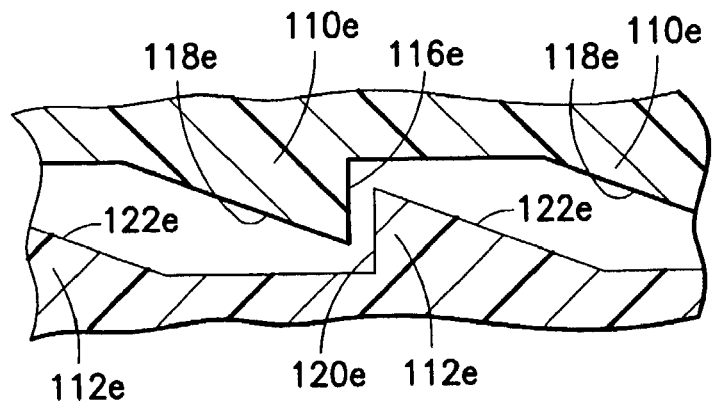
FIG. 30 is a detail cross sectional view of detail A from FIG. 29.
Figure 31:
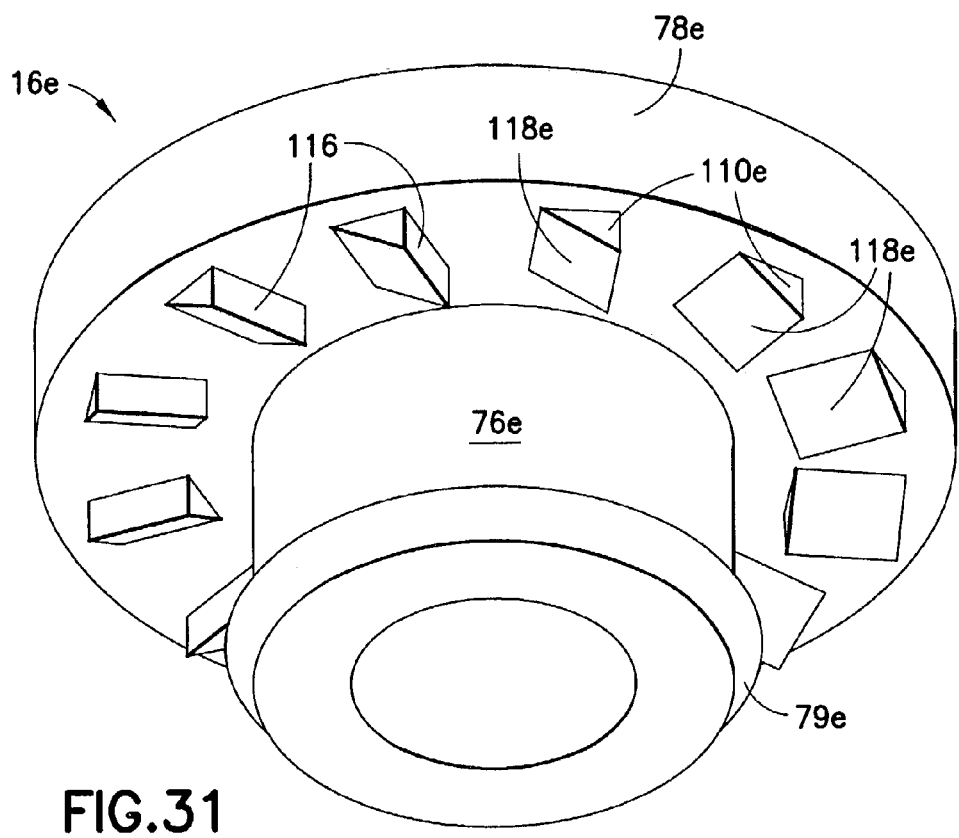
FIG. 31 is a perspective view of the collar of FIGS. 27–29.
Figure 32:
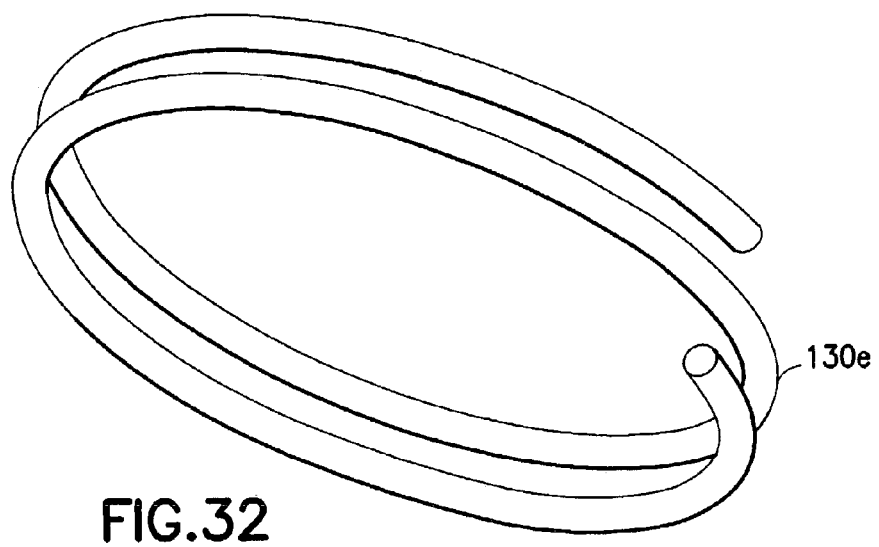
FIG. 32 is a perspective view of an extension spring used in the fifth embodiment of the medical needle device of FIG. 27.

Referring to FIGS. 20 and 21, a further embodiment of the medical needle device of the present invention is shown. The medical needle device of FIGS. 20–21 differs from the medical needle device 10a of FIGS. 1–11 in that the ratchet teeth (70a) formed on the inner surface of the holder body are replaced by a second set of locking pawls 100c. The locking pawls 80c on the second disc portion 78c co-act with the ratchet pawls 100c formed on the inner surface 54c of the wall of the holder body in the same manner as the locking teeth 70a discussed previously in connection with FIGS. 1–11. FIG. 21 shows a close-up view of the engagement of the locking pawls 80c on the second disc portion 78c of the collar with the ratchet pawls 100c extending from the inner surface 54c of the wall of the holder body. The end faces 82c of the locking pawls 80c on the second disc portion 78c, contact end faces 102c of the ratchet pawls 100c extending from the inner surface 54c to prevent rotational movement of the needle assembly and collar relative to the holder. The ratchet pawls 100c further include inward facing surfaces 104c that slidably contact the outward facing surfaces 88c of the locking pawls 80c extending from the second disc portion 78c, which permits rotational movement of the needle assembly and the collar in the opposite direction. Accordingly, operation of the medical needle device in the embodiment of FIGS. 20–21 is identical to the medical needle devices 10a and 10b discussed previously.

FIGS. 22–26 show the medical needle device according to yet a further embodiment of the present invention. The medical needle device is similar to the embodiments discussed previously, with the exception that both second disc portion 78d and the holder body 40d are formed with oppositely engaging ratchet teeth. In particular, the holder body 40d is formed in a similar manner to the holder body 10a of FIGS. 1–11, with the inner surface 54d of the wall 52d of the holder body 40d having a plurality of ratchet teeth 70d. The second disc portion 78d of the collar 16d is now formed in a similar manner to the collar 16b of the medical needle device 10b of FIGS. 14–19 and includes a plurality of locking teeth 80d. Thus, the locking teeth 80d on the second disc portion 78d are oriented to engage the ratchet teeth 70d formed on the inner surface 54d of the wall 52d of the holder body 40d of the medical needle device. The ratchet teeth 70d include inward facing surfaces 86d that slidably engage outward facing surfaces 88d of the locking teeth 80d to permit rotational movement of the needle assembly 12d and collar 16d relative to the holder 14d. The end faces 82d of the locking teeth 80d engage end faces 84d of the ratchet teeth 80d in a similar manner to the various embodiments of the medical needle device discussed previously to prevent rotational movement of the needle assembly 12d and collar 16d relative to the holder 14d. The medical needle device of FIGS. 22–26 operates in an identical manner to the medical needle devices discussed previously in connection with FIGS. 1–21.

FIGS. 27–32 show the medical needle device according to a further embodiment in which the medical needle device is formed slightly different from the earlier discussed embodiments. In this embodiment, a plurality of locking teeth 110e depend from the second disc portion 78e and face the inner side 72e of the distal end face 46e of the holder body 40e. The depending locking teeth 110e are configured to engage a plurality of ratchet teeth 112e formed on the inner side 72e of the distal end face 46e of the holder body 40e. Each of the depending locking teeth 110e include a flat engaging surface 116e and an inclined sliding surface 118e. The ratchet teeth 112e are formed in a similar manner, each having a flat engaging surface 120e in a slanted or inclined sliding surface 122e. The engaging surfaces 116e of the locking teeth 110e face the engaging surfaces 120e of the ratchet teeth 112e so that only one-way rotational motion is permitted between the needle assembly 12e and the collar 16e and the holder 14e. Accordingly, the sliding surfaces 118e of the locking teeth 110e and ratchet teeth face sliding surfaces 122e to permit the one-way rotational movement of the collar 16e relative to the holder 14e.

To facilitate the engagement of the locking teeth 110e with the ratchet teeth 112e, a compression element such as an extension spring 130e is provided about the first disc portion 76e of the collar 16e. The compression element may be any structure or element which is capable of providing an outward biasing force to bias the lip 79e formed on the first disc portion 76e away from the distal end face 46e of the holder body 40e. This may be achieved, for example, through a compression spring, a spring washer, a flexibly resilient projection extending inward from the distal end face 46e, or the like. For purposes of description, the compression element is described in terms of extension spring 130e.

The extension spring 130e provides outward biasing force to bias the lip 79e formed on the first disc portion 76e away from the distal end face 46e of the holder body 40e. This causes the locking teeth 110e to engage the ratchet teeth 112e and permit the one-way rotational movement needle assemble 12e and collar 16e relative to the holder 14e. The extension spring 130e is compressed between the distal end face 46e of the holder body 40e and the lip 79e on the first disc portion 76e of the collar 16e. The extension spring 130e provides sufficient outward biasing force between the lip 79e and the distal end face 46e of the holder body 40e so that the needle hub 18e may be threaded into engagement within the opening 90e (needle hub receiving socket) without the locking teeth 110e becoming disengaged (i.e. separated) from the ratchet teeth 112e. However, the sliding surfaces 118e, 122e of the locking teeth 110e and ratchet teeth 112e prevent the unthreading of the needle hub 18e from the opening 90e if the user of the medical needle device attempts to unthread the needle hub 18e from the opening 90e. Thus, the principle of operation of the medical needle device in this embodiment is similar to the previously discussed medical needle devices, with only the location of the locking teeth 110e and ratchet teeth 112e being changed.

In summary, the medical needle device of the present invention allows a needle assembly to be threadably engaged with a one-way rotational collar. Once the needle assembly is threadably engaged in the collar, the various "slip-disc" schemes identified hereinabove in connection with the embodiments of the present invention prevent the needle assembly from being unthreaded from the collar. Thus, a user of the medical needle device of the present invention is prevented from tampering with the needle assembly such as attempting to remove the needle assembly from the holder at the conclusion of a blood collection or other bodily fluid collection procedure.

We claim:

1. A holder for supporting a needle assembly for use in a blood collection procedure comprising:
   a hollow holder body having a generally open proximal end and a partially enclosed distal end, with the distal end of the holder body defining an opening communicating with the interior of the holder body; and
   a one-way rotatable collar in rotational communication with the opening in the holder body and including a needle assembly receiving socket for receiving a needle assembly for connection with the holder body;
   wherein the collar is configured to co-act with the interior of the holder body such that the collar can rotate in only one direction relative to the holder body when a needle assembly is received in the socket.

2. The holder of claim 1, wherein the collar includes a first disc portion rotatably received in the opening in the holder body and a second disc portion extending into the interior of the holder body, and wherein the second disc portion includes at least one locking pawl configured to engage at least one ratchet tooth formed on an inner wall of the holder body for permitting the one-way rotational movement of the collar relative to the holder body.

3. The holder of claim 2, wherein the first disc portion includes a lip in engagement with the distal end of the holder body for rotatably connecting the collar to the holder body.

4. The holder of claim 2, wherein the socket includes internal threads for threaded engagement with the needle assembly.

5. The holder of claim 4, wherein the locking pawl and the ratchet tooth are configured to engage when the needle assembly is being threaded into the socket to prevent rotation of the collar, with the locking pawl and ratchet tooth further configured to allow the locking pawl to slip over the ratchet tooth to rotate the collar when the needle assembly is threaded with the socket and an attempt is made to unthread the needle assembly from the socket.

6. The holder of claim 1, wherein the proximal end of the holder body is open-ended and includes a circumferentially extending flange.

7. The holder of claim 6, wherein the flange includes two projections.

8. The holder of claim 1, wherein the collar includes a first disc portion rotatably received in the opening in the holder body and a second disc portion extending into the interior of the holder body, and wherein the second disc portion includes at least one locking tooth configured to engage at least one ratchet pawl formed on an inner wall of the holder body for permitting the one-way rotational movement of the collar relative to the holder body.

9. The holder of claim 8, wherein the first disc portion includes a lip in engagement with the distal end of the holder body for rotatably connecting the collar to the holder body.

10. The holder of claim 8, wherein the socket includes internal threads for threaded engagement with the needle assembly.

11. The holder of claim 10, wherein the locking pawl and the ratchet tooth are configured to engage when the needle assembly is being threaded into the socket to prevent rotation of the collar, with the locking pawl and ratchet tooth further configured to allow the locking pawl to slip over the ratchet tooth to rotate the collar when the needle assembly is threaded with the socket and an attempt is made to unthread the needle assembly from the socket.

12. The holder of claim 1, wherein the collar includes a first disc portion rotatably received in the opening in the holder body and a second disc portion extending into the interior of the holder body, and wherein the second disc portion includes at least one locking pawl configured to engage at least one ratchet pawl formed on an inner wall of the holder body for permitting the one-way rotational movement of the collar relative to the holder body.

13. The holder of claim 12, wherein the first disc portion includes a lip in engagement with the distal end of the holder body for rotatably connecting the collar to the holder body.

14. The holder of claim 12, wherein the socket includes internal threads for threaded engagement with the needle assembly.

15. The holder of claim 14, wherein the locking pawl and the ratchet pawl on the inner wall of the holder body are configured to engage when the needle assembly is being threaded into the socket to prevent rotation of the collar, with the locking pawl and the ratchet pawl on the inner wall of the holder body further configured to allow the locking pawl to slip over the ratchet pawl to rotate the collar when the needle assembly is threaded with the socket and an attempt is made to unthread the needle assembly from the socket.

16. The holder of claim 1, wherein the collar includes a first disc portion rotatably received in the opening in the holder body and a second disc portion extending into the interior of the holder body, and wherein the second disc portion includes at least one locking tooth configured to engage at least one ratchet tooth formed on an inner wall of the holder body for permitting the one-way rotational movement of the collar relative to the holder body.

17. The holder of claim 16, wherein the first disc portion includes a lip in engagement with the distal end of the holder body for rotatably connecting the collar to the holder body.

18. The holder of claim 16, wherein the socket includes internal threads for threaded engagement with the needle assembly.

19. The holder of claim 18, wherein the locking tooth and the ratchet tooth on the inner wall of the holder body are configured to engage when the needle assembly is being threaded into the socket to prevent rotation of the collar, with the locking tooth and the ratchet tooth on the inner wall of the holder body further configured to allow the locking tooth to slip over the ratchet tooth to rotate the collar when the needle assembly is threaded with the socket and an attempt is made to unthread the needle assembly from the socket.

20. The holder of claim 1, wherein the collar includes a first disc portion rotatably received in the opening in the holder body and a second larger diameter disc portion extending into the interior of the holder body, and wherein the second disc portion includes at least one locking tooth facing the inner surface of the distal end of the holder body and configured to engage at least one tooth formed on the inner surface of the distal end of the holder body for permitting the one-way rotational movement of the collar relative to the holder body.

21. The holder of claim 20, wherein the socket includes internal threads for threaded engagement with the needle assembly.

22. The holder of claim 20, wherein the first disc portion includes a lip at a distal end thereof, with the holder further including a compression element positioned about the first disc portion between the lip and the distal end surface of the holder body for biasing the lip away from the distal end surface of the holder body and causing the locking tooth to engage the ratchet tooth and permit the one-way rotational movement of the collar relative to the holder body.

23. The holder of claim 22, wherein the compression element is a coil compression spring.

24. The holder of claim 21, wherein the first disc portion includes a lip at a distal end thereof, with the medical needle device further including a compression element positioned about the first disc portion between the lip and the distal end surface of the holder body for biasing the lip away from the distal end surface of the holder body and causing the locking tooth to engage the ratchet tooth and permit the one-way rotational movement of the collar relative to the holder body, and wherein the compression element provides sufficient outward biasing force such that the needle assembly may be threaded into engagement with the socket without the locking tooth becoming disengaged from the ratchet tooth.

25. A holder for use with a medical needle assembly including a needle hub and a needle, comprising:
  a hollow holder body having a proximal end and a distal end, with the distal end defining an opening communicating with the interior of the holder;
  a one-way rotatable collar in rotational communication with the opening in the holder body for connecting the needle assembly to the holder body, with the collar defined by a first disc portion rotatably received in the opening in the holder body and a second disc portion extending into the interior of the holder body, with the collar defining a needle assembly receiving socket;
  wherein the second disc portion of the collar is configured to co-act with the interior of the holder body such that the collar can rotate in only one direction relative to the holder body.

26. The holder of claim 25, wherein the first disc portion includes a lip in engagement with the distal end of the holder body for rotatably connecting the collar to the holder body.

27. The holder of claim 25, wherein the socket is internally threaded to receive an externally threaded needle hub.

28. A method of using a medical needle device in a blood collection procedure, comprising the steps of:
  (a) providing a medical needle assembly including an externally threaded needle hub and a needle supported by the hub;
  (b) providing a holder for the needle assembly including a hollow holder body having an end defining an opening communicating with the interior of the holder, and a one-way rotatable collar in rotational communication with the opening in the holder body, the collar including an internally threaded needle hub receiving socket;
  (c) threading the needle hub into the socket of the collar in one rotational direction; and
  (d) preventing the needle hub from being unthreaded from the socket once fully threaded into the socket in the collar.

29. The method of claim 28, wherein the collar is defined by a first disc portion rotatably received in the opening in the holder body and a second disc portion extending into the interior of the holder body, and wherein the second disc portion includes at least one locking pawl configured to engage at least one ratchet tooth formed on an inner wall of the holder body such that step (d) is performed by the locking pawl rotationally engaging the ratchet tooth on the inner wall of the holder body.

30. The method of claim 28, wherein the collar is defined by a first disc portion rotatably received in the opening in the holder body and a second disc portion extending into the interior of the holder body, and wherein the second disc portion includes at least one locking tooth configured to engage at least one ratchet pawl formed on an inner wall of the holder body such that step (d) is performed by the locking tooth rotationally engaging the ratchet pawl on the inner wall of the holder body.

31. The method of claim 28, wherein the collar is defined by a first disc portion rotatably received in the opening in the holder body and a second disc portion extending into the interior of the holder body, and wherein the second disc portion includes at least one locking pawl configured to engage at least one ratchet pawl formed on an inner wall of the holder body such that step (d) is performed by the locking pawl rotationally engaging the ratchet pawl on the inner wall of the holder body.

32. The method of claim 28, wherein the collar is defined by a first disc portion rotatably received in the opening in the holder body and a second disc portion extending into the interior of the holder body, and wherein the second disc portion includes at least one locking tooth configured to engage at least one ratchet tooth formed on an inner wall of the holder such that step (d) is performed by the locking tooth rotationally engaging the ratchet tooth on the inner wall of the holder body.

33. A holder assembly for receiving a medical needle supported by a hub and for guiding a collection container into piercable engagement with the needle, the holder assembly comprising:
  a hollow body comprising a tubular wall extending along an axis between an open end for receiving a collection container and a partially enclosed end, the hollow body including at least one tooth extending from the tubular wall; and
  a selectively rotatable needle mount engaged with the partially enclosed end of the body and comprising a bore with an internal thread spiraling in a first direction about the axis, the rotatable needle mount including at least one tooth for interference engagement with the at least one tooth of the hollow body when the needle mount is rotated in the first direction, the interference engagement causing sufficient resistance for a hub supporting a needle to be threaded with the internal thread of the needle mount, the interference engagement being insufficient to cause unthreading of a hub threaded with the internal thread of the needle mount when the needle mount is rotated in a direction opposite the first direction.

34. A medical needle device, comprising:
a needle assembly including a needle hub supporting a needle, with the needle hub having a proximal end and a distal end;
a hollow needle assembly holder having a proximal end and a distal end, with the distal end of the holder defining an opening communicating with the interior of the holder; and
a one-way rotatable collar in rotational communication with the opening in the holder for connecting the needle assembly to the holder, with the collar defining a needle assembly receiving socket, and with the proximal end of the needle hub received in the socket;
wherein the collar is configured to co-act with the interior of the holder such that the collar and needle assembly can rotate in only one direction relative to the holder.

35. The medical needle device of claim 34, wherein the collar includes a first disc portion rotatably received in the opening in the holder and a second disc portion extending into the interior of the holder body, and wherein the second disc portion includes at least one locking pawl configured to engage at least one ratchet tooth formed on an inner wall of the holder for permitting the one-way rotational movement of the collar relative to the holder.

36. The medical needle device of claim 35, wherein the first disc portion includes a lip in engagement with the distal end of the holder for rotatably connecting the collar to the holder.

37. The medical needle device of claim 35, wherein the proximal end of the needle hub is externally threaded and the socket is internally threaded such that the needle assembly is held in the socket by a threaded connection.

38. The medical needle device of claim 37, wherein the locking pawl and the ratchet tooth are configured to engage when the needle hub is threaded into the socket, with the locking pawl and ratchet tooth further configured to allow the locking pawl to slip over the ratchet tooth if a user of the medical needle device attempts to unthread the needle hub from the socket.

39. The medical needle device of claim 34, wherein the needle is supported by the proximal end of the needle hub and extends into the interior of the holder for connection to a bodily fluid collection tube.

40. The medical needle device of claim 34, wherein the needle is supported by the needle hub with a proximal end of the needle extending into the interior of the holder for connection to a bodily fluid collection tube and a distal end of the needle projecting outward from the holder for insertion into the body of a patient.

41. The medical needle device of claim 40, further including a sleeve extending from the proximal end of the needle hub and covering the proximal end of the needle.

42. The medical needle device of claim 40, wherein the proximal end and the distal end of the needle comprise separate first and second needles.

43. The medical needle device of claim 34, wherein the needle is supported by the proximal end of the needle hub and extends into the interior of the holder for connection to a bodily fluid collection tube, and wherein the distal end of the needle hub is a male luer.

44. The medical needle device of claim 43, further including a sleeve extending from the proximal end of the needle hub and covering the proximal end of the needle.

45. The medical needle device of claim 34, wherein the needle hub, holder, and collar are made of molded plastic.

46. The medical needle device of claim 34, wherein the collar includes a first disc portion rotatably received in the opening in the holder and a second disc portion extending into the interior of the holder, and wherein the second disc portion includes at least one locking element configured to engage at least one ratchet element formed on an inner wall of the holder for permitting the one-way rotational movement of the collar relative to the holder.

47. The medical needle device of claim 46, wherein the first disc portion includes a lip in engagement with the distal end of the holder for rotatably connecting the collar to the holder.

48. The medical needle device of claim 46, wherein the proximal end of the needle hub is externally threaded and the socket is internally threaded such that the needle assembly is held in the socket by a threaded connection.

49. The medical needle device of claim 48, wherein the locking element and the ratchet element on the inner wall of the holder are configured to engage when the needle hub is threaded into the socket, with the locking element and ratchet element further configured to allow the locking element to slip over the ratchet element if a user of the medical needle device attempts to unthread the needle hub from the socket.

* * * * *